US007687641B2

(12) United States Patent
Jordan et al.

(10) Patent No.: US 7,687,641 B2
(45) Date of Patent: Mar. 30, 2010

(54) CHEMICALS, COMPOSITIONS, AND METHODS FOR TREATMENT AND PREVENTION OF ORTHOPOXVIRUS INFECTIONS AND ASSOCIATED DISEASES

(75) Inventors: Robert F Jordan, Corvallis, OR (US); Thomas R. Bailey, Phoenixville, PA (US); Susan R. Rippin, Wilmington, DE (US); Dongcheng Dai, Corvallis, OR (US)

(73) Assignee: Siga Technologies, Inc., New York, NY (US)

( * ) Notice: Subject to any disclaimer, the term of this patent is extended or adjusted under 35 U.S.C. 154(b) by 101 days.

(21) Appl. No.: 11/785,997

(22) Filed: Apr. 23, 2007

(65) Prior Publication Data

US 2008/0004452 A1 Jan. 3, 2008

Related U.S. Application Data

(63) Continuation-in-part of application No. 10/561,153, filed as application No. PCT/US2004/019552 on Jun. 18, 2004.

(60) Provisional application No. 60/480,182, filed on Jun. 20, 2003.

(51) Int. Cl.
*C07D 209/56* (2006.01)

(52) U.S. Cl. ........................................................ 548/424

(58) Field of Classification Search .................. 548/424
See application file for complete search history.

(56) References Cited

U.S. PATENT DOCUMENTS

| | | | |
|---|---|---|---|
| 4,029,666 | A | 6/1977 | Weber et al. |
| 4,061,763 | A | 12/1977 | Shepard et al. |
| 4,173,646 | A | 11/1979 | Shepard et al. |
| 2007/0254934 | A1 | 11/2007 | Hruby et al. |
| 2007/0287735 | A1 | 12/2007 | Jordan et al. |
| 2008/0103181 | A9 | 5/2008 | Jordan et al. |

OTHER PUBLICATIONS

Ishitobi et al. "Re-examination of the Cycloaddition of Cycloheptatriene with Maleic Anhydrid" Bulletin of the Chemical Society of Japan, vol. 44, 2993-3000 (1971).

Co-pending U.S. Appl. No. 10/561,153, filed Apr. 5, 2006, inventor(s) Robert F. Jordan et al.

Continuation-in-part Co-pending U.S. Appl. No. 11/785,998, filed Apr. 23, 2007, inventor(s) Robert F. Jordan et al.

*Primary Examiner*—Rei-tsang Shiao
(74) *Attorney, Agent, or Firm*—Kramer Levin Naftalis & Frankel LLP

(57) ABSTRACT

Methods of using di, tri, and tetracyclic acylhydrazide derivatives and analogs, as well as pharmaceutical compositions containing the same, for the treatment or prophylaxis of viral infections and diseases associated therewith, particularly those viral infections and associated diseases cased by the orthopoxvirus.

10 Claims, No Drawings

CHEMICALS, COMPOSITIONS, AND METHODS FOR TREATMENT AND PREVENTION OF ORTHOPOXVIRUS INFECTIONS AND ASSOCIATED DISEASES

This application is a Continuation-in-Part of U.S. application Ser. No. 10/561,153, filed Apr. 5, 2006, which claims priority to International Patent Application Serial No. PCT/2004/112718, filed Jun. 18, 2004, which claims priority to U.S. Provisional Application No. 60/480,182, filed Jun. 20, 2003. All priority applications in their entireties are incorporated by reference herein for all purposes.

FIELD

Described herein are di, tri, and tetracyclic acylhydrazide derivatives and analogs, as well as compositions containing the same, for the treatment or prophylaxis of viral infections and diseases associated therewith, particularly those viral infections and associated diseases caused by the orthopoxvirus.

BACKGROUND

The *Orthopox* genus (*Orthopoxviridae*) is a member of the Poxviridae family and the Chordopoxivirinae subfamily. The genus consists of numerous viruses that cause significant disease in human and animal populations. Viruses in the *orthopox* genus include cowpox, monkeypox, vaccinia, and variola (smallpox), all of which can infect humans.

The smallpox (variola) virus is of particular importance. Recent concerns over the use of smallpox virus as a biological weapon have underscored the necessity of developing small molecule therapeutics that target orthopoxviruses. Variola virus is highly transmissible and causes severe disease in humans resulting in high mortality rates (Henderson et al. (1999) JAMA. 281:2127-2137). Moreover, there is precedent for use of variola virus as a biological weapon. During the French and Indian wars (1754-1765), British soldiers distributed blankets used by smallpox patients to American Indians in order to establish epidemics (Stern, E. W. and Stern, A. E. 1945. The effect of smallpox on the destiny of the Amerindian. Boston). The resulting outbreaks caused 50% mortality in some Indian tribes (Stern, E. W. and Stern, A. E.). More recently, the Soviet government launched a program to produce highly virulent weaponized forms of variola in aerosolized suspensions (Henderson, supra). Of more concern is the observation that recombinant forms of poxvirus have been developed that have the potential of causing disease in vaccinated animals (Jackson et al. (2001) J. Virol., 75:1205-1210).

The smallpox vaccine program was terminated in 1972; thus, many individuals are no longer immune to smallpox infection. Even vaccinated individuals may no longer be fully protected, especially against highly virulent or recombinant strains of virus (Downie and McCarthy. (1958) J Hyg. 56:479-487; Jackson, supra). Therefore, mortality rates would be high if variola virus were reintroduced into the human population either deliberately or accidentally.

Variola virus is naturally transmitted via aerosolized droplets to the respiratory mucosa where replication in lymph tissue produces asymptomatic infection that lasts 1-3 days. Virus is disseminated through the lymph to the skin where replication in the small dermal blood vessels and subsequent infection and lysis of adjacent epidermal cells produces skin lesions (Moss, B. (1990) Poxviridae and Their Replication, 2079-2111. In B. N. Fields and D. M. Knipe (eds.), Fields Virology. Raven Press, Ltd., New York). Two forms of disease are associated with variola virus infection; variola major, the most common form of disease, which produces a 30% mortality rate and variola minor, which is less prevalent and rarely leads to death (<1%). Mortality is the result of disseminated intravascular coagulation, hypotension, and cardiovascular collapse, that can be exacerbated by clotting defects in the rare hemorrhagic type of smallpox (Moss, supra).

A recent outbreak of monkeypox virus underscores the need for developing small molecule therapeutics that target viruses in the *orthopox* genus. Appearance of monkeypox in the US represents an emerging infection. Monkeypox and smallpox cause similar diseases in humans, however mortality for monkeypox is lower (1%).

Vaccination is the current means for preventing orthopox virus disease, particularly smallpox disease. The smallpox vaccine was developed using attenuated strains of vaccinia virus that replicate locally and provide protective immunity against variola virus in greater than 95% of vaccinated individuals (Modlin (2001) MMWR (Morb Mort Wkly Rep) 50:1-25). Adverse advents associated with vaccination occur frequently (1:5000) and include generalized vaccinia and inadvertent transfer of vaccinia from the vaccination site. More serious complications such as encephalitis occur at a rate of 1:300,000, which are often fatal (Modlin, supra). The risk of adverse events is even more pronounced in immunocompromised individuals (Engler et al. (2002) J Allergy Clin Immunol. 110:357-365). Thus, vaccination is contraindicated for people with AIDS or allergic skin diseases (Engler et al.). While protective -immunity lasts for many years, the antibody response to smallpox vaccination is significantly reduced 10 to 15 years post inoculation (Downie, supra). In addition, vaccination may not be protective against recombinant forms of orthopoxvirus. A recent study showed that recombinant forms of mousepox virus that express IL-4 cause death in vaccinated mice (Jackson, supra). Given the side effects associated with vaccination, contraindication of immunocompromised individuals, and inability to protect against recombinant strains of virus, better preventatives and/or new therapeutics for treatment of smallpox virus infection are needed.

Vaccinia virus immunoglobulin (VIG) has been used for the treatment of post-vaccination complications. VIG is an isotonic sterile solution of immunoglobulin fraction of plasma derived from individuals who received the vaccinia virus vaccine. It is used to treat eczema vaccinatum and some forms of progressive vaccinia. Since this product is available in limited quantities and difficult to obtain, it has not been indicated for use in the event of a generalized smallpox outbreak (Modlin, supra).

Cidofovir ([(S)-1-(3-hydroxy-2-phosphonylmethoxypropyl)cytosine] [HBMPC]) is a nucleoside analog approved for treatment of CMV retinitis in AIDS patients. Cidofovir has been shown to have activity in vitro against a number of DNA containing viruses including adenovirus, herpesviruses, hepadnaviruses, polyomaviruses, papillomaviruses, and orthopoxviruses (Bronson et al. (1990) Adv. Exp. Med. Biol. 278: 277-83; De Clercq et al. (1987) Antiviral Res. 8:261-272; de Oliveira et al. (1996) Antiviral Res. 31:165-172; Snoeck et al. (2001) Clin Infect. Dis. 33:597-602). Cidofovir has also been found to inhibit authentic variola virus replication (Smee et al. (2002) Antimicrob. Agents Chemother. 46:1329-1335).

However, cidofovir administration is associated with a number of issues. Cidofovir is poorly bioavailable and must be administered intravenously (Laezari et al. (1997) Ann. Intern. Med. 126:257-263). Moreover, cidofovir produces dose-limiting nephrotoxicity upon intravenous administration (Lalezari et al.). In addition, cidofovir-resistance has been noted for multiple viruses. Cidofovir-resistant cowpox, monkeypox, vaccinia, and camelpox virus variants have been isolated in the laboratory by repeated passage in the presence of drug (Smee, supra). Cidofovir-resistance represents a significant limitation for use of this compound to treat orthopoxvirus replication. Thus, the poor bioavailability, need for intravenous administration, and prevalence of resistant virus underscores the need for development of additional and alternative therapies to treat orthopoxvirus infection.

In addition to viral polymerase inhibitors such as cidofovir, a number of other compounds have been reported to inhibit orthopoxvirus replication (De Clercq. (2001) Clin Microbiol. Rev. 14:382-397). Historically, methisazone, the prototypical thiosemicarbazone, has been used in the prophylactic treatment of smallpox infections (Bauer et al. (1969) Am. J Epidemiol. 90:130-145). However, this compound class has not garnered much attention since the eradication of smallpox due to generally unacceptable side effects such as severe nausea and vomiting. Mechanism of action studies suggest that methisazone interferes with translation of L genes (De Clercq (2001), supra). Like cidofovir, methisazone is a relatively non-specific antiviral compound and can inhibit a number of other viruses including adenoviruses, picornaviruses, reoviruses, arboviruses, and myxoviruses (Id.).

Another class of compounds potentially useful for the treatment of poxviruses is represented by inhibitors of S-adenosylhomocysteine hydrolase (SAH). This enzyme is responsible for the conversion of S-adenosylhomocysteine to adenosine and homocysteine, a necessary step in the methylation and maturation of viral mRNA. Inhibitors of this enzyme have shown efficacy at inhibiting vaccinia virus in vitro and in vivo (De Clercq et al. (1998) Nucleosides Nucleotides. 17:625-634.). Structurally, all active inhibitors reported to date are analogues of the nucleoside adenosine. Many are carbocyclic derivatives, exemplified by Neplanacin A and 3-Deazaneplanacin A. While these compounds have shown some efficacy in animal models, like many nucleoside analogues, they suffer from general toxicity and/or poor pharmacokinetic properties (Coulombe et al. (1995) Eur. J Drug Metab Pharmacokinet. 20:197-202; Obara et al. (1996) J Med. Chem. 39:3847-3852). It is unlikely that these compounds can be administered orally, and it is currently unclear whether they can act prophylactically against smallpox infections. Identification of non-nucleoside inhibitors of SAH hydrolase, and other chemically tractable variola virus genome targets that are orally bioavailable and possess desirable pharmacokinetic (PK) and absorption, distribution, metabolism, excretion (ADME) properties would be a significant improvement over the reported nucleoside analogues. In summary, currently available compounds that inhibit smallpox virus replication are generally non-specific and suffer from use limiting toxicities and/or questionable efficacies.

In U.S. Pat. No. 6,433,016 (Aug. 13, 2002) and U.S. Application Publication 2002/0193443 A1 (published Dec. 19, 2002) a series of imidodisulfamide derivatives are described as being useful for orthopoxvirus infections.

New therapies and preventatives are clearly needed for infections and diseases caused by orthopoxvirus infection.

Several orthopoxviruses, including cowpox, monkeypox, camelpox, variola, and probably most other mammalian orthopoxviruses, can be grown readily in cell culture and produce robust cytopathic effect (CPE) in 3 to 5 days. Since this CPE is directly related to viral replication, compounds that inhibit virus replication in cell culture can be identified readily as conferring protection from virus-induced CPE (although it is theoretically possible to inhibit CPE without inhibiting virus replication). Moreover, compounds having identified activity against cowpox virus will also likely be active against human variola virus given the high degree of homology (>95%) between these two viruses and the fact that the replication proteins of orthopoxviruses are highly homologous. In general, the viruses diverge in regions of their genomes that encode immunomodulatory functions (host-specific). Additionally, many compounds have been identified in the literature that inhibit orthopoxvirus replication in cell culture and there are few, if any, examples where a compound is dramatically more potent against one species of orthopoxvirus and not the others

SUMMARY

Described herein are compounds and compositions and/or methods for the treatment and prophylaxis of viral infections, as well as diseases associated with viral infections in living hosts. The compounds described herein are of the following general formula:

I

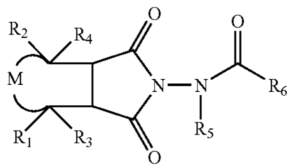

wherein:

$R_1$ and $R_2$ represent radicals independently selected from the group consisting of hydrogen and alkyl;

$R_3$ and $R_4$ represent radicals independently selected from the group consisting of hydrogen and alkyl;

or $R_3$ and $R_4$ taken together with the carbons to which they are attached form a cyclic structure selected from the group consisting of

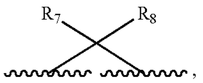,

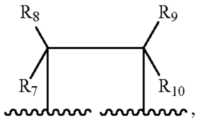,

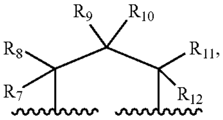,

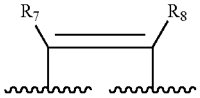,

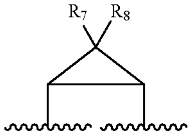, and

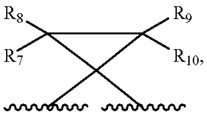, wherein $R_7$, $R_8$, $R_9$, $R_{10}$, $R_{11}$, and $R_{12}$ represent radicals that are independently selected from the group consisting of hydrogen and alkyl;

$R_5$ represents a radical selected from the group consisting of hydrogen and alkyl;

$R_6$ represents a radical selected from the group consisting of straight- or branched chain alkyl, cycloalkyl, cycloalkylalkyl, alkenyl, alkynyl, cycloalkenyl, a substituted or unsubstituted aryl group, a substituted or unsubstituted heteroaryl group selected from the group consisting of furyl, thienyl, pyridyl, pyrrolyl, oxazolyl, thiazolyl, imidazolyl, pyrazolyl, isoxazolyl, isothiazolyl, 1,2,3-oxadiazolyl, 1,2,3-triazolyl, and tetrazolyl; a substituted or unsubstituted arylalkyl group, and a substituted or unsubstituted heteroarylalkyl group, wherein the heteroaryl is selected from the group consisting pyridine and thiophene;

M is selected from the group consisting of

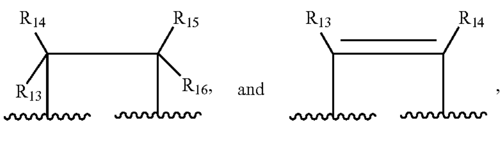

wherein $R_{13}$, $R_{14}$, $R_{15}$, and $R_{16}$ are independently selected from the group consisting of hydrogen and alkyl;

said aryl group substituents and said arylalkyl group substituents being one or more radical(s) independently selected from the group consisting of a straight- or branched chain alkyl, alkoxy, alkoxyalkyl, alkoxyalkoxy, halogen, polyfluoroalkyl, polyfluoroalkoxy, carboxy, cyano, nitro, amido, amidoalkyl, carboxamide, alkylthio, alkylsulfinyl, alkylsulfonyl, sulfonamide, and mercapto;

said heteroaryl group substituents and said heteroarylalkyl group substituents being one or more radical(s) independently selected from the group consisting of a straight- or branched chain alkyl, hydroxy, alkoxy, alkoxyalkyl, alkoxyalkoxy, halogen, polyfluoroalkyl, polyfluoroalkoxy, carboxy, cyano, amino, monoalkylamino, dialkylamino, aminoalkyl, nitro, amido, amidoalkyl, carboxamide, alkylthio, alkylsulfinyl, alkylsulfonyl, sulfonamide, and mercapto;

or a pharmaceutically acceptable salt thereof.

Also described herein are pharmaceutical compositions containing the antiviral compounds of Formula I and the corresponding methods of use for treating and preventing infections caused by orthopox viruses.

DETAILED DESCRIPTION

Described herein are compounds of Formula I:

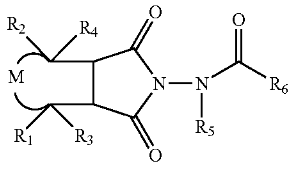

wherein $R_1$, $R_2$, $R_3$, $R_4$, $R_5$, $R_6$, and M are as defined above, with the proviso that said formula does not include the compounds selected from the group consisting of N-(3,3a,4,4a,5,5a,6,6a-octahydro-1,3-dioxo-4,6-ethenocycloprop[f]isoindol - - - 2(1H)-yl-4-pyridinecarboxamide; 4-bromo-N-(3,3a,4,4a,5,5a,6,6a-octahydro-1,3-dioxo-4,6-ethenocycloprop[f]-isoindol-2(1H)-yl)-benzamide; 3-bromo-N-(3,3a,4,4a,5,5a,6,6a-octahydro-1,3-dioxo-4,6-ethenocycloprop[f]-isoindol-2(1H)-yl)-benzamide; 3-chloro-N-(3,3a,4,4a,5,5a,6,6a-octahydro-1,3-dioxo-4,6-ethenocycloprop[f-]isoindol-2(1H)-yl)-benzamide; N-(3,3a,4,4a,5,5a,6,6a-octahydro-1,3-dioxo-4,6-ethenocycloprop[f]-isoindol-2(1-yl)-4-pyridinecarboxamide; 4-bromo-N-(3,3a,4,4a,5,5a,6,6a-octahydro-1,3-dioxo-4,6-ethenocycloprop[f]-isoindol-2(1H)-yl)-benzamide; 4-methoxy-N-(3,3a,4,4a,5,5a,6,6a-octahydro-1,3-dioxo-4,6-ethenocycloprop[-f]isoindol-2(1H)-yl)-benzamide; 4-bromo-N-(3,3a,4,4a,5,5a,6,6a-octahydro-1,3-dioxo-4,6-ethanocycloprop[f]-isoindol-2(1H)-yl)-benzamide; 3-bromo-N-(1',3',3'a,4',7',7'a-hexahydro-1',3'-dioxospiro[cyclopropane-1,8'-[4,7]methano[2H]isoindol]-2'-yl)-benzamide; N-(3,3a,4,4a,5,5a,6,6a-octahydro-1,3-dioxo-4,6-ethenocycloprop[f]isoindol- -2(1H)-yl)-tricyclo[3.3.1.13,7]decane-1-carboxamide and 4-bromo-N-(1,3,3a,4,7,7a-hexahydro-1,3-dioxo-4,7-methano-2H-isoindol-2-yl)-benzamide.

Compounds of Formula I include the compounds of Formula Ia:

Ia

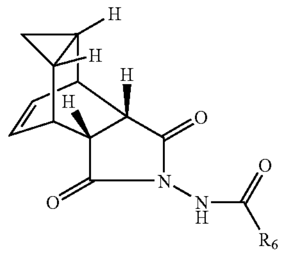

wherein:

$R_6$ represents a radical selected from the group consisting of straight- or branched chain alkyl, cycloalkyl, cycloalkylalkyl, alkenyl, alkynyl, cycloalkenyl, a substituted or unsubstituted aryl group, a substituted or unsubstituted heteroaryl group selected from the group consisting of furyl, thienyl, pyridyl, pyrrolyl, oxazolyl, thiazolyl, imidazolyl, pyrazolyl, isoxazolyl, isothiazolyl, 1,2,3-oxadiazolyl, 1,2,3-triazolyl, and tetrazolyl; a substituted or unsubstituted arylalkyl group, and a substituted or unsubstituted heteroarylalkyl group, wherein the heteroaryl is selected from the group consisting pyridine and thiophene;

said aryl group substituents and said arylalkyl group substituents being one or more radical(s) independently selected from the group consisting of a straight- or branched chain alkyl, alkoxy, alkoxyalkyl, alkoxyalkoxy, halogen, polyfluoroalkyl, polyfluoroalkoxy, carboxy, cyano, nitro, amido, amidoalkyl, carboxamide, alkylthio, alkylsulfinyl, alkylsulfonyl, sulfonamide, and mercapto;

said heteroaryl group substituents and said heteroarylalkyl group substituents being one or more radical(s) independently selected from the group consisting of a straight- or branched chain alkyl, hydroxy, alkoxy, alkoxyalkyl, alkoxyalkoxy, halogen, polyfluoroalkyl, polyfluoroalkoxy, carboxy, cyano, amino, monoalkylamino, dialkylamino, aminoalkyl, nitro, amido, amidoalkyl, carboxamide, alkylthio, alkylsulfinyl, alkylsulfonyl, sulfonamide, and mercapto;

or a pharmaceutically acceptable salt thereof.

Also described herein are compounds of Formula Ib:

Ib

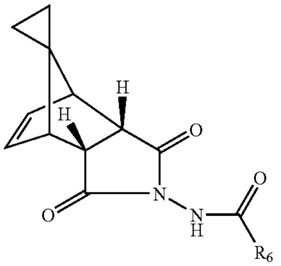

wherein:

$R_6$ represents a radical selected from the group consisting of straight- or branched chain alkyl, cycloalkyl, cycloalkylalkyl, alkenyl, alkynyl, cycloalkenyl, a substituted or unsubstituted aryl group, a substituted or unsubstituted heteroaryl group selected from the group consisting of furyl, thienyl, pyridyl, pyrrolyl, oxazolyl, thiazolyl, imidazolyl, pyrazolyl, isoxazolyl, isothiazolyl, 1,2,3-oxadiazolyl, 1,2,3-triazolyl, and tetrazolyl; a substituted or unsubstituted arylalkyl group, and a substituted or unsubstituted heteroarylalkyl group, wherein the heteroaryl is selected from the group consisting pyridine and thiophene;

said aryl group substituents and said arylalkyl group substituents being one or more radical(s) independently selected from the group consisting of a straight- or branched chain alkyl, alkoxy, alkoxyalkyl, alkoxyalkoxy, halogen, polyfluoroalkyl, polyfluoroalkoxy, carboxy, cyano, nitro, amido, amidoalkyl, carboxamide, alkylthio, alkylsulfinyl, alkylsulfonyl, sulfonamide, and mercapto;

said heteroaryl group substituents and said heteroarylalkyl group substituents being one or more radical(s) independently selected from the group consisting of a straight- or branched chain alkyl, hydroxy, alkoxy, alkoxyalkyl, alkoxyalkoxy, halogen, polyfluoroalkyl, polyfluoroalkoxy, carboxy, cyano, amino, monoalkylamino, dialkylamino, aminoalkyl, nitro, amido, amidoalkyl, carboxamide, alkylthio, alkylsulfinyl, alkylsulfonyl, sulfonamide, and mercapto;

or a pharmaceutically acceptable salt thereof.

Exemplary compounds include 4-trifluoromethyl-N-(3,3a,4,4a,5,5a,6,6a-octahydro-1,3-dioxo-4,6-ethenocycloprop[f]isoindol-2(1H)-yl)-benzamide; 4-bromo-N-(3,3a,4,4a,5,5a,6,6a-octahydro-1,3-dioxo-4,6-ethanocycloprop[f]isoindol-2(1H)-yl)-benzamide; 4-bromo-N-(octahydro-1,3-dioxo-2H-isoindol-2-yl)-benzamide; 4-fluoro-N-(3,3a,4,4a,5,5a,6,6a-octahydro-1,3-dioxo-4,6-ethenocycloprop[f]isoindol-2(1H)-yl)-benzamide; 3-fluoro-N-(3,3a,4,4a,5,5a,6,6a-octahydro-1,3-dioxo-4,6-ethenocycloprop[f]isoindol-2(1H)-yl)-benzamide; N-(3,3a,4,4a,5,5a,6,6a-octahydro-1,3-dioxo-4,6-ethenocycloprop[f]isoindol- -2(1H)-yl)-4-pyridinecarboxamide; 4-bromo-N-(3,3a,4,4a,5,5a,6,6a-octahydro-1,3-dioxo-4,6-ethenocycloprop[f]-isoindol-2(1H)-yl)-benzamide; 4-chloro-N-(3,3a,4,4a,5,5a,6,6a-octahydro-1,3-dioxo-4,6-ethenocycloprop[f]isoindol-2(1H)-yl)-benzamide; 4-trifluoromethyl-N-bicyclo[2.2.2]oct-5-ene-2,3-dicarboximido-benzamide; 4-trifluoromethyl-N-bicyclo[2.2.2]octane-2, 3-dicarboximido-benzamide; and 2,4-dimethyl-N-(3,3a,4,4a,5,5a,6,6a-octahydro-1,3-dioxo-4,6-ethenocycloprop[f]isoindol-2(1H)-yl)-thiazole-5-carboxamide.

Also described herein compounds selected from the group consisting of 4-trifluoromethyl-N-(3,3a,4,4a,5,5a,6,6a-octahydro-1 ,3-dioxo-4,6-ethenocycloprop-[f]isoindol-2(1H)-yl)-benzamide; 2-bromo-N-(3,3a,4,4a,5,5a,6,6a-octahydro-1,3-dioxo-4,6-ethenocycloprop[f]isoindol-2(1H)-yl)-benzamide; N-(3,3a,4,4a,5,5a,6,6a-octahydro-1,3-dioxo-4,6-ethenocycloprop[f]isoindol-2(1H)-yl)-3-pyridinecarboxamide; N-(3,3a,4,4a,5,5a,6,6a-octahydro-1,3-dioxo-4,6-ethenocycloprop[f]isoindol-2(1H)-yl)-2-pyridinecarboxamide; 4-nitro-N-(3,3a,4,4a,5,5a,6,6a-octahydro-1,3-dioxo-4,6-ethenocycloprop[f]isoindol-2(1H)-yl)-benzamide; 4-fluoro-N-(3,3a,4,4a,5,5a,6,6a-octahydro-1,3-dioxo-4,6-ethenocycloprop[f]isoindol-2(1H)-yl)-benzamide; 3-fluoro-N-(3,3a,4,4a,5,5a,6,6a-octahydro-1,3-dioxo-4,6-ethenocycloprop[f]isoindol-2(1H)-yl)-benzamide; 4-bromo-N-(3,3a,4,4a,5,5a,6,6a-octahydro-1,3-dioxo-4,6-ethanocycloprop[f]isoindol-2(1H)-yl)-benzamide; 4-bromo-N-(1,3-(2H,3aH)-dioxo-4,8-ethenocyclohepta[c]pyrrolyl)-benzamide; 4-bromo-N-(octahydro-1,3-dioxo-2H-isoindol-2-yl)-benzamide; 4-bromo-N-bicyclo[2.2.2]oct-5-ene-2,3-dicarboximido-benzamide; 4-bromo-N-bicyclo[2.2.2]octane-2,3-dicarboximido-benzamide; 4-cyano-N-(3,3a,4,4a,5,5a,6,6a-octahydro-1,3-dioxo-4,6-ethenocycloprop[f]-isoindol-2(1H)-yl)-benzamide; 4-trifluoromethyl-N-(3,3a,4,4a,5,5a,6,6a-octahydro-1,3-dioxo-4,6-ethenocy-cloprop[f]isoindol-2(1H)-yl)-benzamide; 4 trifluoromethyl-N-bicyclo[2.2.2]oct-5-ene-2,3-dicarboximido-benzamide; and 4-trifluoromethyl-N-bicyclo[2.2.2]octane-2,3-dicarboximido-benzamide.

The compound may be selected from any of the compounds described, supra.

Also described herein is a method for preventing and treating orthopoxvirus infections and for preventing and treating diseases associated with such infections in a living host (for example, a mammal including a human) having or susceptible to an orthopoxvirus infection, comprising the step of administering to the living host a therapeutically effective amount of a compound of the formula:

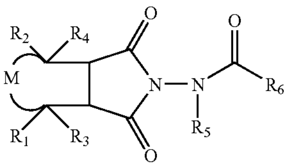

wherein $R_1$, $R_2$, $R_3$, $R_4$, $R_5$, $R_6$, and M are as defined for compounds of Formula I above, or a pharmaceutically acceptable salt to a host susceptible to, or suffering from such infection.

Such methods include the prevention and treatment of orthopoxvirus infections and diseases associated with such infections in a living host having or susceptible to an orthopoxvirus infection, comprising the step of administering a therapeutically effective amount of the compounds of the Formula la, above, or a pharmaceutically acceptable salt thereof. Also described is the prophylaxis or treatment of orthopoxvirus infections and diseases associated with such infections in a living host having or susceptible to an orthopoxvirus infection, comprising the step of administering a therapeutically effective amount of the compounds of the Formula lb, above or a pharmaceutically acceptable salt, thereof.

Also described herein are methods for the treatment or prevention of infections caused by an orthopox virus wherein the orthopox virus is selected from the group consisting of vaccinia virus, cowpox virus, smallpox (variola) virus, monkeypox virus and camelpox virus; in a living host (for example, a mammal including a human) comprising the step of administering a therapeutically effective amount of the compounds of the invention to a host susceptible to, or suffering from such infection.

Also described herein is a pharmaceutical composition for the treatment or prevention of orthopoxvirus infections and diseases associated with such infections in a living host, that comprises a therapeutically effective amount of one or more of the compounds of the formula:

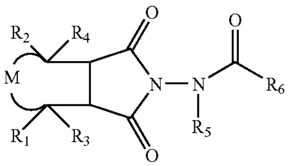

wherein $R_1$, $R_2$, $R_3$, $R_4$, $R_5$, $R_6$, and M are as defined for compounds of Formula I above, and a pharmaceutically acceptable carrier medium.

The compounds described herein, their isomers and pharmaceutically acceptable salts, exhibit antiviral activity. The compounds described herein are particularly effective against orthopoxviruses, and are useful in the prophylaxis and/or treatment of infections and diseases associated with this virus in living hosts. Examples of orthopoxviruses that may be treated or prevented as described herein include, but are not limited to, aractuba virus, BeAn 58058 virus, buffalopox virus, camelpox virus (such as Camelpox virus 903, Camelpox virus CMG, Camelpox virus CMS, Camelpox virus CP1, Camelpox virus CP5, and Camelpox virus M-96), cantagalo orthopoxvirus, cowpox virus (such as Cowpox virus strain Hamburg-1985 and Cowpox virus strain Turkmenia-1974), Ectromelia virus (such as Belo Horizonte virus), elephantpox virus, monkeypox virus (such as Monkeypox virus strain Sierra Leone 70-0266 and Monkeypox virus strain Zaire 77-0666), rabbitpox virus (such as Rabbitpox strain Utrecht), raccoonpox virus, skunkpox virus, taterapox virus, vaccinia virus (including, but not limited to, the following strains: strain Ankara, strain Copenhagan, strain Dairen I, strain IHD-J, strain L-IPV, strain LC16M8, strain LC16MO, strain Lister, strain LIVP, strain Tian Tan, strain WR 65-16, strain WR, and strain Wyeth), Variola virus (such as variola major virus and variola minor virus), and volepox virus.

In vitro cell-based studies have been performed that demonstrate the usefulness of compounds described herein as antiviral agents. For example, antiviral activity of representative compounds was evaluated in assays that measure the ability of compounds to protect cells from virus-induced CPE. Cells that will support growth of the particular orthopox virus strain are seeded into 96-well tissue culture treated plates and then infected with an amount of the appropriate orthopox virus strain that results in complete CPE in about 3 days. Various dilutions of inhibitory compound(s) are added and the plates are incubated at the appropriate temperature for optimal virus growth. At the end of the incubation period, cells are fixed with glutaraldehyde and stained with crystal violet. Cell protection is measured spectrophotometrically at $OD_{570}$ nm. The interpolated compound dilution that results in 50% protection of the cell monolayer from virus-induced CPE is calculated and reported as the 50% effective concentration or $EC_{50}$. Antiviral activity of representative compounds described herein occurred at drug concentrations that had no demonstrable effect on cell growth, indicating that the compounds were working specifically by an antiviral mechanism.

The compounds described herein, collectively, include the compounds of Formula I, pharmaceutically acceptable salts thereof, their isomers, and mixtures thereof. The compounds are identified herein by their chemical structure and/or chemical name. Where a compound is referred to by both a chemical structure and a chemical name, and that chemical structure and chemical name conflict, the chemical structure is determinative of the compound's identity.

The term "living host" as used herein refers to an organism that is living and capable of being infected with a virus, such as an orthopoxvirus; for example, a mammal, which includes a human.

The term "alkyl" as used herein refers to straight or branched chain aliphatic hydrocarbon radicals of up to 10 carbon atoms, preferably up to 6 carbon atoms and more preferably 1 to 4 carbon atoms. Similarly, the term "alkyl", or any variation thereof, used in combination form to name substituents, such as alkoxy (—O-alkyl), allylthio (—S-alkyl), monoalkylamino (—NH-alkyl), dialkylamino (—N-(alkyl)alkyl), alkylsulfonyl (—$S(O)_2$-alkyl), carboxyalkyl (-alkyl-COOH), or the like, also refers to aliphatic hydrocarbon radicals of one to six carbon atoms, and preferably of one to four carbon atoms. Also "alk" in structural formula denotes an alkyl group, unless divalency is indicated in which case the "alk" denotes the corresponding alkylene group(s). Additionally, the term "lower alkyl" denotes an alkyl group having one to four carbon atoms.

The term "alkenyl" as used herein refers to straight or branched chain aliphatic hydrocarbon radicals of 2 to 7 carbon atoms containing one double bond. Such alkenyl moieties may exist in the E or Z configurations; the compounds of this invention include both configurations. The term "alkynyl" as used herein refers to straight or branched chain aliphatic hydrocarbon radicals containing 2 to 7 carbon atoms having at least one triple bond.

The term "phenyl" as used herein refers to a

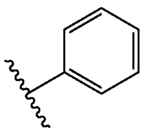

group. A "substituted phenyl" refers to a phenyl group that is substituted with the indicated substituents.

As used herein, the term "aryl", when used as such, refers to an aromatic carbocyclic group, having 6 to 10 carbon atoms including without limitation phenyl and napthyl.

The term "heteroaryl," as used herein, refers to a 5- or 6-membered aromatic cyclic group having at least one carbon atom and one or more oxygen, nitrogen or sulfur atoms in the ring, as for example furyl, thienyl, pyridyl, pyrrolyl, oxazolyl, thiazolyl, imidazolyl, pyrazolyl, isoxazolyl, isothiazolyl, 1,2,3-oxadiazolyl, 1,2,3-triazolyl, tetrazolyl, and the like, including all position isomers. Preferred heteroaryl groups include pyridine, thiazole and thiophene.

As used herein, the term "cycloalkyl" refers to a saturated hydrocarbon ring. Cycloalkyls can be monocyclic or can be fused, spiro or bridged bicyclic or tricyclic ring systems. Monocyclic cycloalkyl rings contain from 3 to 10 carbon atoms, preferably from 3 to 7 carbon atoms, as for example cyclopropyl, cyclobutyl, cyclopentyl, and cyclohexyl. Bicyclic and tricyclic cycloalkyl rings contain from 7 to 28 carbon atoms, preferably from 7 to 19 carbon atoms, in the ring system; and include, for example, adamantyl, bicyclo[2.2.1]heptyl, bicyclo[2.2.2]cyclooctanyl, tricyclo[3.2.2.02,4]nonyl and norbornyl, and bicyclo[3.2.2]nonyl. As used herein, the term "cycloalkenyl" refers to an unsaturated hydrocarbon ring. Cycloalkenyl rings are non-aromatic and contain at least one (preferably only one) carbon-carbon double bond. Cycloalkenyl rings are monocyclic, or are fused, spiro or bridged bicyclic or tricyclic ring systems. Monocyclic cycloalkenyl rings contain from 5 to 10 carbon atoms, preferably from 5 to 7 carbon atoms, and include, for example, cyclopropenyl, cyclobutenyl, cyclopentenyl, and cyclohexenyl. Bicyclic and tricyclic cycloalkenyl rings contain from 7 to 28 carbon atoms in the ring, preferably from 7 to 19 carbon atoms, in the ring system; and include, for example, bicyclo[2.2.1]hept-2-ene, bicyclo[2.2.2]cyclooct-2-enyl, tricyclo[3.2.2.02,4]non-6-enyl, and bicyclo[3.2.2]non-6-enyl.

The term "amido," as used herein, refers to a radical or substituent of the formula —NR"C(═O)R"', wherein R" and R"' represent hydrogen or alkyl.

The term "carboxamide," as used herein, refers to a radical or substituent of the formula —C(═O)—NR"R"', wherein R" and R"' are as previously defined.

The term "sulfonamide," as used herein, refers to a radical or substituent of the formula —$SO_2$NR"R"' or —NR"$SO_2$R"', wherein R" and R"'are as previously defined.

The term "halogen," as used herein, refers to a radical or substituent selected from the group consisting of chloro, bromo, iodo, and fluoro.

The term "HPLC," as used herein, refers to high-performance liquid chromatography.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is an oxo (═O) group, then 2 hydrogens on the atom are replaced.

The compounds described herein and their pharmaceutically acceptable salts are useful in treating and preventing viral infections and diseases in living hosts when used in combination with other active agents, including but not limited to interferons, ribavirin, immunoglobulins, immunomodulators, anti-inflammatory agents, antibiotics, antivirals, anti-infectious agents, and the like.

Compounds described herein are also useful in preventing or resolving orthopox viral infections in cell, tissue or organ cultures and other in vitro applications. For example, inclusion of compounds of the invention as a supplement in cell or tissue culture growth media and cell or tissue culture components will prevent viral infections or contaminations of cultures not previously infected with viruses. Compounds described above may also be used to eliminate or attenuate viral replication in cultures or other biological materials infected or contaminated with viruses (for example, blood), after a suitable treatment period, under any number of treatment conditions as determined by the skilled artisan.

The compounds described herein can form useful salts with inorganic and organic acids such as hydrochloric, sulfuric, acetic, lactic, or the like and with inorganic or organic bases such as sodium or potassium hydroxide, piperidine, ammonium hydroxide, or the like. The pharmaceutically acceptable salts of the compounds of Formula I are prepared following procedures that are familiar to those skilled in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

To the extent that certain compounds described herein may have at least one chiral center, the compounds may thus exist as enantiomers. In addition, the compounds described herein may also possess two or more chiral centers and thus may also exist as diastereomers or as exo or endo isomers. Where the processes for the preparation of the present compounds give rise to a mixture of stereoisomers, these isomers may be separated by conventional techniques such as preparative chromatography. Accordingly, the compounds may be prepared as a racemic mixture or, by either enantiospecific synthesis or resolution, as individual enantiomers. The compounds may, for example, be resolved from a racemic mixture into their component racemates by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The racemic mixture may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope described herein.

The compounds described herein are useful for treating orthopoxvirus infection in living hosts, for example, mammals including humans. When administered to a living host the compounds can be used alone, or as a pharmaceutical composition.

Pharmaceutical compositions comprising the compounds described herein, either alone or in combination with each other, offer a treatment against orthopoxvirus infection. The antiviral pharmaceutical compositions described herein comprise one or more of the compound(s) of Formula I above, as the active ingredient in combination with a pharmaceutically acceptable carrier medium or auxiliary agent.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier medium" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Twentieth Edition, A. R. Gennaro (William and Wilkins, Baltimore, Md., 2000) discloses various carriers used in formulating pharmaceutical compositions and known techniques for the preparation thereof. Except insofar as any conventional carrier medium is incompatible with the antiviral compounds of the invention, such as by producing any undesirable biological effect or otherwise interacting in a deleterious manner with any other component(s) of the pharmaceutical composition, its use is contemplated to be within the scope of the compositions described herein.

In the pharmaceutical compositions described herein, the active agent may be present in an amount of at least 0.5% and generally not more than 90% by weight, based on the total weight of the composition, including carrier medium and/or auxiliary agent(s), if any. Typically, the proportion of active agent varies between 5 to 50% by weight of the composition.

Pharmaceutical organic or inorganic solid or liquid carrier media suitable for enteral or parenteral administration can be used to make up the composition. Gelatine, lactose, starch, magnesium stearate, talc, vegetable and animal fats and oils, gum, polyalkylene glycol, or other known medicament components may all be suitable as carrier media or excipients.

The compounds described herein may be administered using any amount and any route of administration effective for attenuating infectivity of the virus. Thus, the expression "amount effective to attenuate infectivity of virus," as used herein, refers to a nontoxic but sufficient amount of the antiviral agent to provide the desired prophylaxis and/or treatment of viral infection. The exact amount required will vary from subject to subject, depending on the species, age, and general condition of the subject, the severity of the infection, the particular antiviral agent, its mode of administration, and the like.

The compounds described herein may be administered within 24 hours of symptom onset, although therapeutic effects may be produced with administration within 48 hours of symptom onset, or even within 72 hours of symptom onset. Symptoms of initial orthopoxvirus infections depend on the exact virus contracted. For example, the initial symptoms of a smallpox infection include fever, malaise, head and body aches, and sometimes vomiting.

The antiviral compounds may be formulated in dosage unit form for ease of administration and uniformity of dosage. "Dosage unit form," as used herein, refers to a physically discrete unit of antiviral agent appropriate for the patient to be treated. Each dosage should contain the quantity of active material calculated to produce the desired therapeutic effect either as such, or in association with the selected pharmaceutical carrier medium and/or the supplemental active agent(s), if any. Typically, the antiviral compounds of the invention will be administered in dosage units containing from about 100 mg to about 2,000 mg of the antiviral agent by weight of the composition, although dosage units containing from about 10 mg up to about 10,000 mg may also be employed.

The compounds may be administered orally, rectally, parenterally, such as by intramuscular injection, subcutaneous injection, intravenous infusion or the like, intracisternally, intravaginally, intraperitoneally, locally, such as by powders, ointments, or drops, or the like, or by inhalation, such as by aerosol or the like, taking into account the nature and severity of the infection being treated. Depending on the route of administration, the compounds of the invention may be administered at dosage levels of about 0.125 to about 250 mg/kg of subject body weight per dose, one or more times a day, to obtain the desired therapeutic effect.

The compounds of the invention will typically be administered from 1 to 4 times a day so as to deliver the above-mentioned daily dosage. However, the exact regimen for administration of the compounds and compositions described herein will necessarily be dependent on the needs of the individual host or patient being treated, the type of treatment administered and the judgment of the attending medical specialist.

For prophylaxis, compounds of the invention may be administered within 48 hours after possible exposure, although effective prophylaxis can be produced by administration within 7 days post exposure, up to as long as 14 days post exposure. The dosages may be essentially the same, whether for treatment or prophylaxis of virus infection.

During any of the processes for preparation of the compounds described herein, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1999. The protecting groups may be removed at a convenient subsequent stage using methods known from the art.

The following examples are provided to describe the invention in further detail. These examples illustrate suitable methods of synthesis of representative compounds of this invention. However, the methods of synthesis are intended to illustrate and not to limit the invention to those exemplified below. The starting materials for preparing the compounds of the invention are either commercially available or can be conveniently prepared according to one of the examples set forth below or otherwise using known chemistry procedures.

EXAMPLE 1

Preparation of 4-trifluoromethyl-N-(3,3a,4,4a,5,5a,6,6a-octahydro-1,3-dioxo-4,6-ethenocycloprop[f]isoindol-2(1H)-yl)-benzamide ("ST-246")

a. Preparation of Compound 1(a).

1(a)

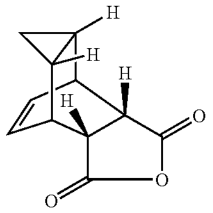

A mixture of cycloheptatriene (5 g, 54.26 mmol) and maleic anhydride (6.13 g, 62.40 mmol) in xylenes (35 mL) was heated at reflux under argon overnight. The reaction was cooled to room temperature and a tan precipitate was collected by filtration and dried to give 2.94 grams (28%) of the desired product.

b. Preparation of ST-246. A mixture of compound 1 (a) (150 mg, 0.788 mmol) and 4-trifloromethylbenzhydrazide (169 mg, 0.827 mmol) in ethanol (10 mL) was heated under argon overnight. The solvent was removed by rotary evaporation. Purification by column chromatography on silica gel using 1/1 hexane/ethyl acetate provided 152 mg (51%) of the product as a white solid.

EXAMPLES 2-14

The compounds of Examples 2-14 were synthesized following the above mentioned general procedure for Example 1 using compound 1(a) and reacting it with the following hydrazides: isonicotinic hydrazide, 4-bromobenzoic hydrazide, 3-bromobenzoic hydrazide, 3-chlorobenzoic hydrazide, 2-bromobenzoic hydrazide, 2-chlorobenzoic hydrazide, 4-chlorobenzoic hydrazide, nicotinic hydrazide, 2-picolinyl hydrazide, 4-methoxybenzoic hydrazide, 4-nitrobenzoic hydrazide, 4-fluorobenzoic hydrazide, and 3-fluorobenzoic hydrazide.

EXAMPLE 15

Preparation of 4-bromo-N-(3,3a,4,4a,5,5a,6,6a-octahydro-1,3-dioxo-4,6-ethanocycloprop[f]-isoindol-2(1H)-yl)-benzamide a. Preparation of Compound 15(a). 15(a)

15(a)

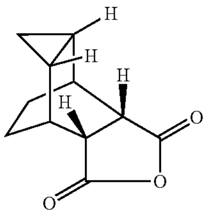

To a solution of compound 1(a) (1 g, 5.26 mmol) in ethanol (20 mL) was added 10% palladium on activated carbon (100 mg, 10 wt %). The mixture was shaken on a Parr hydrogenator under an atmosphere of hydrogen at 50 psi for 3 hours. The mixture was filtered through a micron filter to remove the palladium, and the filtrate was concentrated to give 384 mg (38%) of the product as a white solid.

b. Preparation of 4-bromo-N-(3,3a,4,4a,5,5a,6,6a-octahydro-1,3-dioxo-4,6-ethanocycloprop[f]-isoindol-2(1H)-yl)-benzamide. A mixture of compound 15(a) (350 mg, 1.82 mmol) and 4-bromobenzoic hydrazide (411 mg, 1.91 mmol) in ethanol (10 mL) was heated under argon for 48 hours. The solvent was removed by rotary evaporation. Purification by column chromatography on silica gel using 1/1 hexane/ethyl acetate as eluent provided 444 mg (63%) of the product as a white solid.

EXAMPLE 16

Preparation of 4-bromo-N-(1,3-(2H,3aH)-dioxo-4,8-ethenocyclohepta[c]pyrrolyl)-benzamide a. Preparation of Compound 16(a).

16(a)

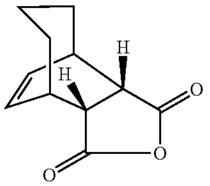

A mixture of 1,3-cycloheptadiene (0.87 mL, 10.62 mmol) and maleic anhydride (1.2 g, 12.24 mmol) in xylenes (7 mL) was heated at reflux under argon overnight. The reaction was cooled to room temperature, and a tan precipitate was collected by filtration and dried to give 1.59 grams (78%) of the desired product.

b. Preparation of 4-bromo-N-(1,3-(2H,3aH)-dioxo-4,8-ethenocyclohepta[c]prrolyl)-benzamide. A mixture of compound 16(a) (500 mg, 2.6 mmol) and 4-bromobenzoic hydrazide (587 mg, 2.73 mmol) in ethanol (5 mL) was heated under argon overnight. The solvent was removed by rotary evaporation. Purification by column chromatography on silica gel using 1/1 hexane/ethyl acetate provided 683 mg (67%) of the product as a white solid.

EXAMPLE 17

Preparation of 4-bromo-N-(octahydro-1,3-dioxo-2H-isoindol-2-yl)-benzamide

A mixture of cis-cyclohexanedicarboxylic anhydride (150 mg, 0.97 mmol) and 4-bromobenzoic hydrazide (220 mg, 1.02 mmol) in ethanol (10 mL) was heated under argon overnight. The solvent was removed via rotary evaporation. Purification by column chromatography on silica gel using 1/1 hexane/ethyl acetate as eluent provided 179 mg (52%) of the desired product as a white solid.

EXAMPLE 18

Preparation of 4-bromo-N-bicyclo[2.2.2]oct-5-ene-2,3-dicarboximido-benzamide a. Preparation of Compound 18(a).

18(a)

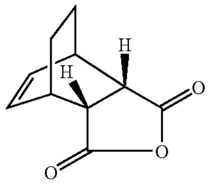

A mixture of 1,3-cyclohexadiene (2.4 mL, 24.96 mmol) and maleic anhydride (2.81 g, 28.66 mmol) in xylenes (15 mL) was heated at reflux overnight. The solution was cooled to room temperature and the precipitate was collected by suction filtration. The solid was washed with xylenes and dried to give 3.08 g (69%) of the product as a tan solid.

b. Preparation of compound 4-bromo-N-bicyclo[2.2.2]oct-5-ene-2,3-dicarboximido-benzamide. A mixture of compound 18(a) (150 mg, 0.84 mmol) and 4-bromobenzoic hydrazide (190 mg, 0.88 mmol) in ethanol (10 mL) was heated under argon overnight. The solvent was removed by rotary evaporation. Purification by column chromatography on silica gel using 1/1 hexane/ethyl acetate gave 210 mg (67%) of the product as a white solid.

EXAMPLES 19-40

(See Tables 1 and 2 below for listed compound names and structures)

EXAMPLE 41

Preparation of 2,4-Dimethyl-N-(3,3a,4,4a,5,5a,6,6a-octahydro-1,3-dioxo-4,6-ethenocycloprop[f]isoindol-2(1R)-yl)-thiazole-5-carboxamide A mixture of compound 1 (a)(150 mg, 0.788 mmol) and 2,4-dimethylthiazole-5-carboxylic acid hydrazide (141 mg, 0.827 mmol) in ethanol (10 mL) was heated at reflux under argon overnight. The solution was then cooled to room temperature, and the white precipitate was collected by filtration. The solid was washed with ethanol, and air-dried affording 183 mg (68%) of the product as a white solid.

By appropriate selection of suitable starting materials, other compounds of the invention may be prepared according to the procedures described in the foregoing examples. Representative examples of further di, tri, and tetracyclic acylhydrazide derivatives and analogues are set forth in Tables 1 and 2 below.

TABLE 1

| Example Number | $R_6$ | *NMR | **Mass Spec | Name |
|---|---|---|---|---|
| 1 | 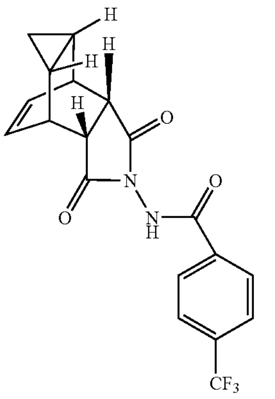 | $^1$H NMR in DMSO-$d_6$: δ 11.35 (d, 1 H): 11.09 (d, 1 H); 8.08 (d, 2 H); 7.92 (d, 2 H); 5.799 (s, 2 H); 3.29 (brs, 4 H), 1.17 (m, 2 H); 0.26 (m, 1 H; 0.078 (s, 1 H) | 375 (M − H)− | 4-Trifluoromethyl-N-(3,3a,4,4a,5,5a,6,6a,-octahydro-1,3-dioxo-4,6-ethenocycloprop[f]isoindol-2(1H)-yl)-benzamide |
| 2 | 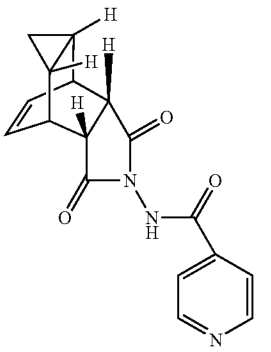 | $^1$H NMR in DMSO-$d_6$: δ 11.41 (brs); 11.15 (brs); 8.77 (d of d, 2 H); 7.75 (d, 2 H); 5.77 (brs, 2 H); 3.27 (brs, 4 H), 1.15 (brs, 2 H); 0.25 (m, 1 H; 0.03 (brs, 1 H) | 308 (M − H)− | N-(3,3a,4,4a,5,5a,6,6a,-octahydro-1,3-dioxo-4,6-ethenocycloprop[f]isoindol-2(1H)-yl)-4-pyridinecarboxamide |
| 3 | 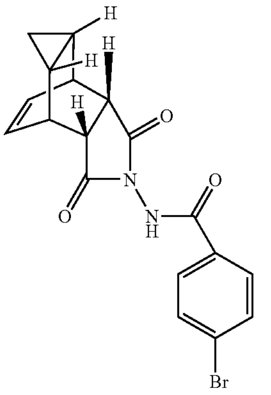 | *** | 385 (M − H)− | 4-Bromo-N-(3,3a,4,4a,5,5a,6,6a,-octahydro-1,3-dioxo-4,6-ethenocycloprop[f]isoindol-2(1H)-yl)-benzamide |
| 4 | 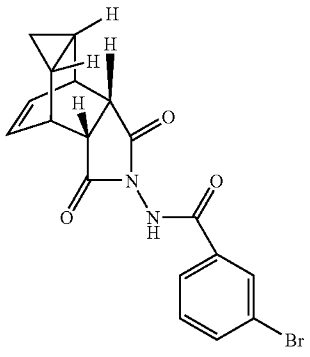 | $^1$H NMR in DMSO-$d_6$: δ 11.13 (brd, 1 H); 10.89 (brd, 1 H); 7.99 (s, 1 H); 7.82-7.76 (m, 2 H); 7.43 (t, 1 H); 5.72(s, 2 H), 3.22-3.08 (m, 4 H); 1.19 (brs, 2 H; 0.21 (m, 1 H); 0.17 (brs, 1 H) | 385 (M − H)− | 3-Bromo-N-(3,3a,4,4a,5,5a,6,6a,-octahydro-1,3-dioxo-4,6-ethenocycloprop[f]isoindol-2(1H)-yl)-benzamide |

TABLE 1-continued

| Example Number | $R_6$ | *NMR | **Mass Spec | Name |
|---|---|---|---|---|
| 5 | 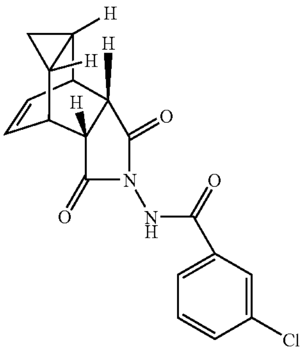 | $^1$H NMR in DMSO-$d_6$: δ 11.21 (brd, 1 H); 10.98 (brd, 1 H); 7.92 (s, 1 H); 7.85 (d, 1 H); 7.71 (d, 1 H); 7.58 (t, 1 H), 5.79 (brs, 2 H); 3.29-3.15 (m, 4 H); 1.19-1.15 (m, 2 H); 0.26 (m, 1 H); 0.10 (brs, 1 H) | 341 (M − H)− | 3-Chloro-N-(3,3a,4,4a,5,5a,6,6a,-octahydro-1,3-dioxo-4,6-ethenocycloprop[f]isoindol-2(1H)-yl)-benzamide |
| 6 | 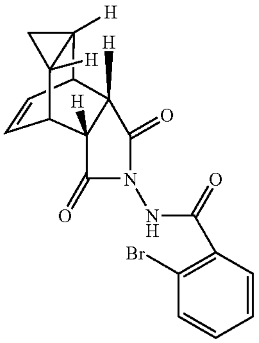 | $^1$H NMR in $CDCl_3$: δ 7.74 (s, 1 H); 7.69 (d, 1 H); 7.63 (d, 1 H); 7.41-7.31 (m, 2 H); 5.84 (m, 2 H); 3.48 (m, 2 H), 3.14 (s, 2 H); 1.19 (m, 2 H); 0.38-0.20 (m, 2 H) | 385 (M − H−) | 2-Bromo-N-(3,3a,4,4a,5,5a,6,6a,-octahydro-1,3-dioxo-4,6-ethenocycloprop[f]isoindol-2(1H)-yl)-benzamide |
| 7 | 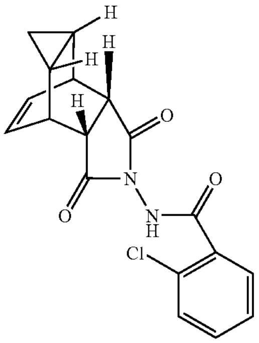 | $^1$H NMR in $CDCl_3$: δ 7.96 (s, 1 H); 7.83 (d, 1 H); 7.45 (m, 2 H); 7.36 (m, 1 H); 5.86 (d, 2 H); 3.47 (brs, 2 H), 3.15 (s, 2 H); 1.15 (brs, 2 H); 0.39-0.20 (m, 2 H) | 341 (M − H)− | 2-Chloro-N-(3,3a,4,4a,5,5a,6,6a,-octahydro-1,3-dioxo-4,6-ethenocycloprop[f]isoindol-2(1H)-yl)-benzamide |
| 8 | 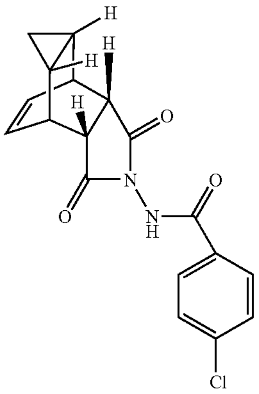 | $^1$H NMR in DMSO-$d_6$: δ 11.16 (brd, 1 H); 10.91 (brd, 1 H); 7.90 (d, 2 H); 7.61 (d, 2 H); 5.79 (s, 2 H); 3.28 (m, 4 H), 1.17 (s, 2 H); 0.26 (m, 1 H); 0.07 (s, 2 H) | 341 (M − )H− | 4-Chloro-N-(3,3a,4,4a,5,5a,6,6a,-octahydro-1,3-dioxo-4,6-ethenocycloprop[f]isoindol-2(1H)-yl)-benzamide |

TABLE 1-continued

| Example Number | $R_6$ | *NMR | **Mass Spec | Name |
|---|---|---|---|---|
| 9 | 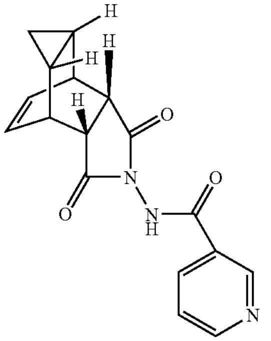 | $^1$H NMR in DMSO-$d_6$: δ 11.33 (brd, 1 H); 9.04 (s, 1 H); 8.8 (m, 1 H); 8.23 (d, 1 H); 7.56 (m, 1 H); 5.80 (s, 2 H), 3.29 (m, 4 H); 1.17 (m, 2 H); 0.27 (m, 1 H); 0.07 (s, 1 H) | 308 (M−)H− | N-(3,3a,4,4a,5,5a,6,6a,-octahydro-1,3-dioxo-4,6-ethenocycloprop[f]isoindol-2(1H)-yl)-3-pyridinecarboxamide |
| 10 | 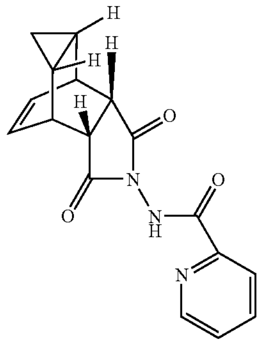 | $^1$H NMR in DMSO-$d_6$: δ 11.11 (s, 1 H); 8.70 (d, 1 H); 8.07-8.02 (M, 2 H); 7.7-7.66 (m, 1 H); 5.75 (m, 2 H); 3.295 (s, 4 H), 1.16 (m, 2 H); 0.27 (m, 1 H); 0.10 (s, 1 H) | 308 (M − H)− | N-(3,3a,4,4a,5,5a,6,6a,-octahydro-1,3-dioxo-4,6-ethenocycloprop[f]isoindol-2(1H)-yl)-2-pyridinecarboxamide |
| 11 | 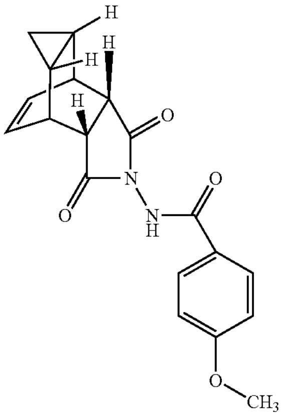 | $^1$NMR in DMSO-$d_6$: δ 10.87 (brd, 1 H); 7.87 (d, 2 H); 7.05 (d, 2 H); 5.78 (br, 2 H); 3.84 (s, 3 H); 3.30 (s, 4 H), 1.16 (m, 2 H); 0.25 (m, 1 H); 0.07 (brs, 1 H) | 339 (M + H)+ | 4-Methoxy-N-(3,3a,4,4a,5,5a,6,6a,-octahydro-1,3-dioxo-4,6-ethenocycloprop[f]isoindol-2(1H)-yl)-benzamide |
| 12 | 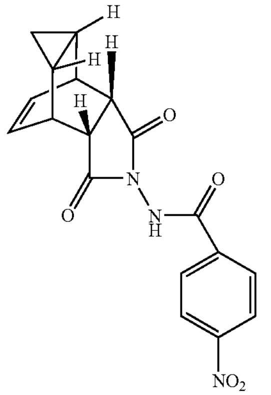 | $^1$H NMR in DMSO-$d_6$: δ 11.537-11.469 (brd, 1 H); 8.38(d, 2 H); 8.12 (d, 2 H); 5.80 (s, 2 H); 3.3 (br, 4 H); 1.18 (s, 2 H); 0.27 (m, 1 H); 0.08 (s, 1 H) | 352 (M − H)− | 4-Nitro-N-(3,3a,4,4a,5,5a,6,6a,-octahydro-1,3-dioxo-4,6-ethenocycloprop[f]isoindol-2(1H)-yl)-benzamide |

TABLE 1-continued

| Example Number | $R_6$ | *NMR | **Mass Spec | Name |
|---|---|---|---|---|
| 13 | 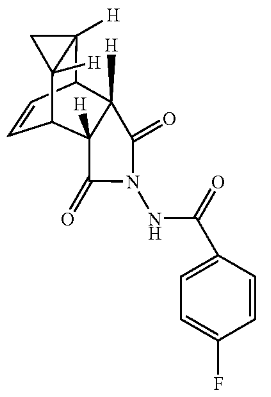 | $^1H$ NMR in DMSO-$d_6$: δ 11.04 (br, 1 H); 7.96 (s, 2 H); 7.367 (t, 2 H); 5.791 (s, 2 H); 3.258 (4 H & $H_2O$), 1.18 (d, 2 H); 0.28 (m, 1 H); 0.09 (s, 1 H) | 327.0 (M + H)+ | 4-Fluoro-N-(3,3a,4,4a,5,5a,6,6a,-octahydro-1,3-dioxo-4,6-ethenocycloprop[f]isoindol-2(1H)-yl)-benzamide |
| 14 | 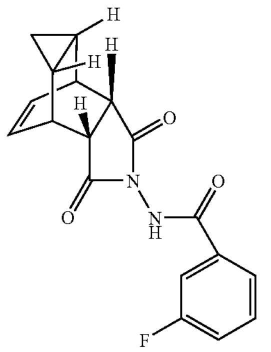 | $^1H$ NMR in DMSO-$d_6$: δ 11.176 (br, 1 H); 7.768-7.459 (m, 4 H); 5.797 (s, 2 H); 3.293 ($H_2O$ & 4 H), 1.174 (s, 2 H); 0.23 (m, 1 H); 0.05 (s, 1 H) | 327.0 (M + H)+ | 3-Fluoro-N-(3,3a,4,4a,5,5a,6,6a,-octahydro-1,3-dioxo-4,6-ethenocycloprop[f]isoindol-2(1H)-yl)-benzamide |
| 15 | 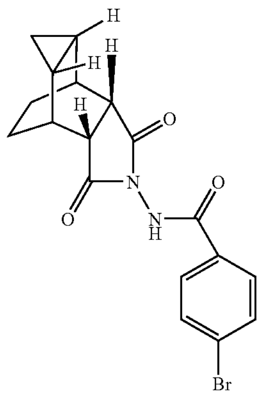 | *** | 388.9 (M − H)− | 4-Bromo-N-(3,3a,4,4a,5,5a,6,6a-octahydro-1,3-dioxo-4,6-ethanocycloprop[f]isoindol-2(1H)-yl)-benzamide |
| 16 | 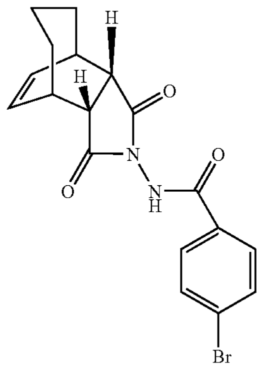 | $^1H$ NMR in DMSO-$d_6$: δ 11.14 (brd, 1 H); 7.85 (brd, 2 H); 7.76 (d, 2 H); 6.10 (brs, 2 H) 3.43 (brd, 2 H), 2.86 (brs, 2 H); 1.98-1.54 (m, 6 H) | 387 (M − H)− | 4-Bromo-N-(1,3-(2H,3aH)-dioxo-4,8-ethenocyclohepta[c]pyrrolyl)-benzamide |

TABLE 1-continued

| Example Number | $R_6$ | *NMR | **Mass Spec | Name |
|---|---|---|---|---|
| 17 | 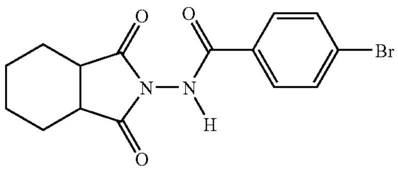 | $^1$H NMR in DMSO-$d_6$: δ 11.16 (s, 1 H); 7.86 (d, 2 H); 7.78 (d, 2 H); 3.147 (brs, 2 H); 1.81-1.68 (brm, 4 H); 1.42 (br, 4 H) | 350.9 $(M + H)^+$ | 4-Bromo-N-(octahydro-1,3-dioxo-2H-isoindol-2-yl)-benzamide |
| 18 | 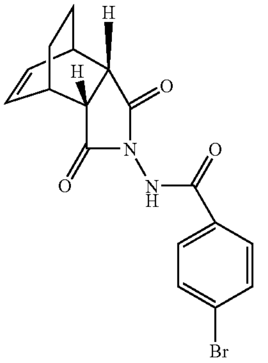 | $^1$H NMR in DMSO-$d_6$: δ 11.05 (brd, 1 H); 7.83 (d, 2 H); 7.76 (d, 2 H); 6.21 (s, 2 H), 3.15 (s, 2 H); 3.04 (s, 2 H); 1.66 (d, 2 H); 1.28 (d, 2 H) | 373 (M − H)− | 4-Bromo-N-bicyclo[2.2.2]oct-5-ene-2,3-dicarboximido-benzamide |
| 19 | 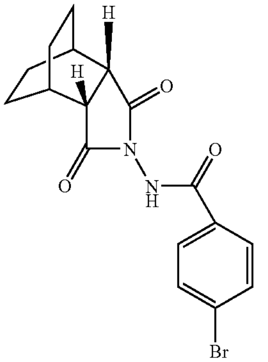 | $^1$H NMR in DMSO-$d_6$: δ 11.15 (s, 1 H); 7.87 (d, 2 H); 7.78 (d, 2 H); 3.07 (m, 2 H), 2.04 (s, 2 H); 1.75-1.64 (m, 2 H); 1.45-1.38 (m, 3 H) | 373 (M − H)− | 4-Bromo-N-bicyclo[2.2.2]octane-2,3-dicarboximido-benzamide |
| 20 | 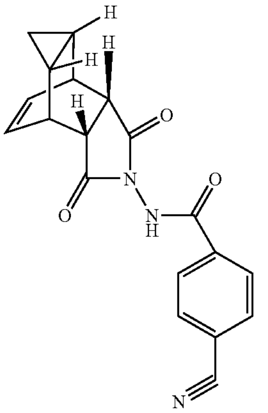 | $^1$H NMR in DMSO-$d_6$: δ 11.36 (br, 1 H); 8.03 (s, 4 H); 5.79 (s, 2 H); 3.30 (4H + $H_2O$); 2.50 (s, 2 H); 1.20 (s, 2 H) | 332.1 (M − H)− | 4-Cyano-N-(3,3a,4,4a,5,5a,6,6a,-octahydro-1,3-dioxo-4,6-ethenocycloprop[f]isoindol-2(1H)-yl)-benzamide |

TABLE 1-continued

| Example Number | $R_6$ | *NMR | **Mass Spec | Name |
|---|---|---|---|---|
| 21 | 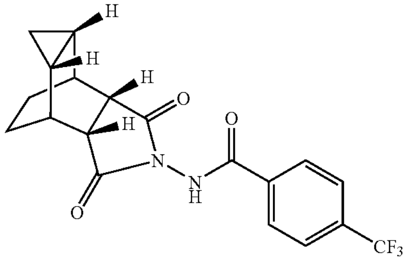 | $^1$H NMR in DMSO-$d_6$: δ 11.286 (br, 1 H); 8.13 (d, 2 H); 8.10 (d, 2 H); 3.30 (4H + $H_2O$); 1.49-1.12 (m, 4 H); 0.83 (s, 1 H); 0.57 (s, 1 H) | 377.0 (M − H)− | 4-Trifluoromethyl-N-(3,3a,4,4a,5,5a,6,6a,-octahydro-1,3-dioxo-4,6-ethanocycloprop[f]isoindol-2(1H)-yl)-benzamide |
| 22 | 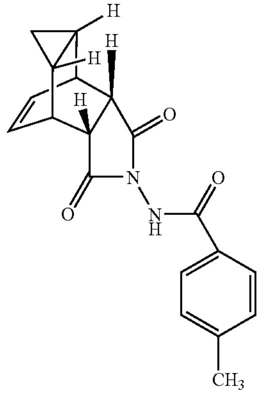 | *** | *** | 4-Methyl-N-(3,3a,4,4a,5,5a,6,6a,-octahydro-1,3-dioxo-4,6-ethenocycloprop[f]isoindol-2(1H)-yl)-benzamide |
| 23 | 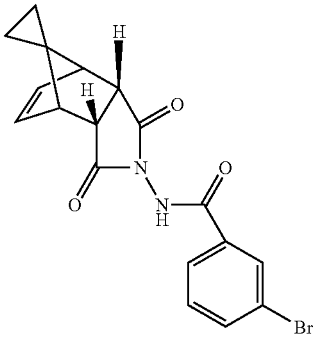 | *** | *** | 3-Bromo-N-(1',3,3'a,4',7,7'a-hexahydro-1',3'-dioxospiro [cyclopropane-1,8'-[4,7] methano[2H]isoindol]-2'-yl)-benzamide |
| 24 | 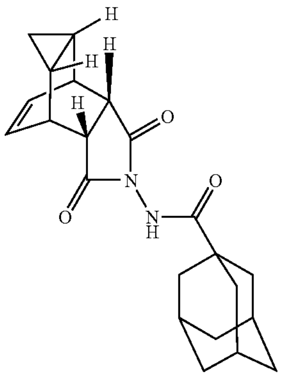 | *** | *** | N-(3,3a,4,4a,5,5a,6,6a,-octahydro-1,3-dioxo-4,6-ethenocycloprop[f]isoindol-2(1H)-yl)-tricyclo[3.3.1.13,7] decane-1-carboxamide |

TABLE 1-continued

| Example Number | $R_6$ | *NMR | **Mass Spec | Name |
|---|---|---|---|---|
| 25 | 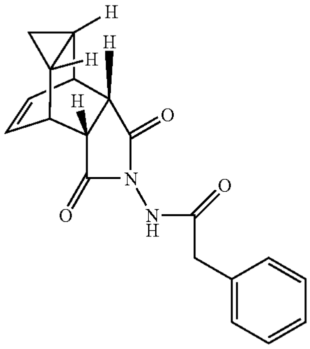 | *** | *** | N-(3,3a,4,4a,5,5a,6,6a,-octahydro-1,3-dioxo-4,6-ethenocycloprop[f]isoindol-2(1H)-yl)-benzeneacetamide |
| 26 | 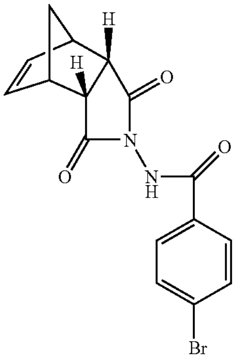 | *** | *** | 4-Bromo-N-(1,3,3a,4,7,7a-hexahydro-1,3,-dioxo-4,7-methano-2H-isoindol-2-yl)-benzamide |
| 27 | 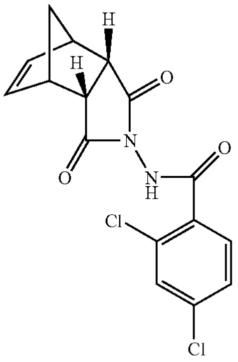 | *** | *** | 2,4-Dichloro-N-(1,3,3a,4,7,7a-hexahydro-1,3,-dioxo-4,7-methano-2H-isoindol-2-yl)-benzamide |
| 28 | 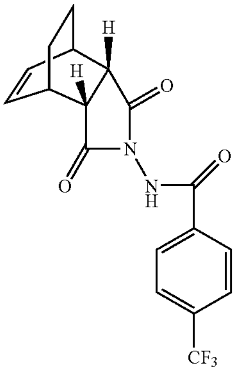 | $^1$H NMR in DMSO-$d_6$: δ 11.37 (br, 1 H); 8.10 (d, 2 H); 7.94 (d, 2 H); 6.22 (s, 2 H); 3.17 (s, 2 H); 3.05 (s, 2 H); 1.66 (m, 2 H); 1.29 (m, 2 H) | 365.0 (M + H)$^+$ | 4-Trifluoromethyl-N-bicyclo [2.2.2]oct-5-ene-2,3-dicarboximido-benzamide |

TABLE 1-continued

| Example Number | $R_6$ | *NMR | **Mass Spec | Name |
|---|---|---|---|---|
| 29 | 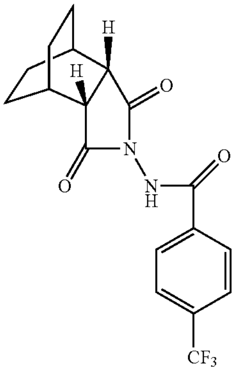 | $^1H$ NMR in DMSO-$d_6$: δ 11.33 (s, 1 H); 8.14 (d, 2 H); 8.11 (d, 2 H); 3.29 (s, 4 H); 2.05 (s, 2 H); 1.76-1.65 (m, 4 H); 1.42 (s, 2 H) | 367.0 $(M + H)^+$ | 4-Trifluoromethyl-N-bicyclo [2.2.2]octane-2,3-dicarboximido-benzamide |

*All 1H NMR and 13C NMR spectra were acquired on a Varian Mercury VX300 Spectrometer and referenced to tetramethysilane (TMS) unless indicated otherwise. Chemical shifts and coupling constants are reported in parts per million (ppm) and Hertz (Hz), respectively, Multiplicities indicated are: s = singlet, d = doublet, t = triplet, q = quartet, m = multiplet, dd = doublet of doublets, and br indicates a broad signal.

**Mass Spectroscopy data is expressed as a mass to charge ratio (m/z) for either (M + 1) or (M − 1) molecular ion.

***indicates that data were not collected.

TABLE 2

| Example Number | Structure | Name |
|---|---|---|
| 30 | 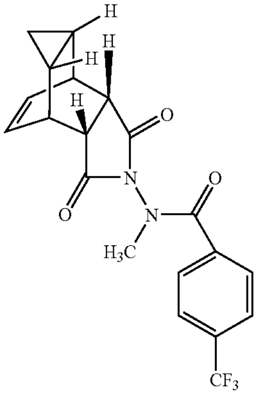 | 4-Trifluoromethyl-N-(3,3a,4,4a,5,5a,6,6a-octahydro-1,3-dioxo-4,6-ethenocycloprop[f]isoindol-2(1H)-yl)-N-methylbenzamide |
| 31 | 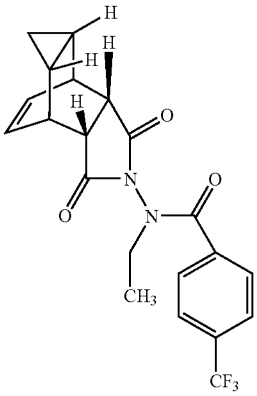 | 4-Trifluoromethyl-N-(3,3a,4,4a,5,5a,6,6a-octahydro-1,3-dioxo-4,6-ethenocycloprop[f]isoindol-2(1H)-yl)-N-ethylbenzamide |

TABLE 2-continued
| | | |
|---|---|---|
| 32 | 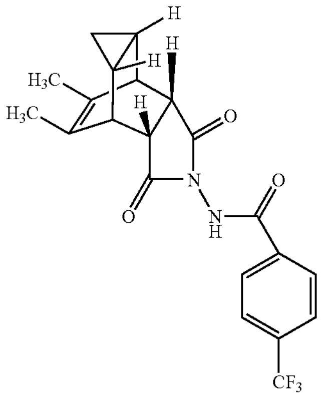 | 4-Trifluoromethyl-N-(3,3a,4,4a,5,5a,6,6a-octahydro-1,3-dioxo-7,8-dimethyl-4,6-ethenocycloprop[f]isoindol-2(1H)-yl)-benzamide |
| 33 | 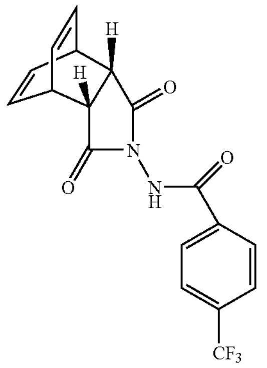 | 4-Trifluoromethyl-N-(3a,4,7,7a-tetrahydro-4,7-etheno-1H-isoindol-2(1H)-yl)-benzamide |
| 34 | 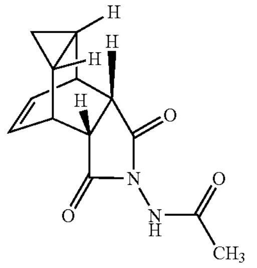 | N-(3,3a,4,4a,5,5a,6,6a-octahydro-1,3-dioxo-7,8-dimethyl-4,6-ethenocycloprop[f]isoindol-2(1H)-yl)-acetamide |
| 35 | 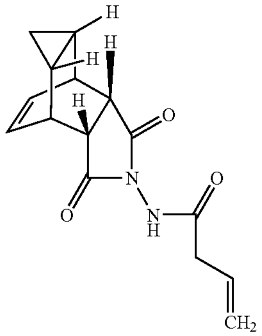 | N-(3,3a,4,4a,5,5a,6,6a-octahydro-1,3-dioxo-7,8-dimethyl-4,6-ethenocycloprop[f]isoindol-2(1H)-yl)-but-3-enamide |

TABLE 2-continued

| | | |
|---|---|---|
| 36 | 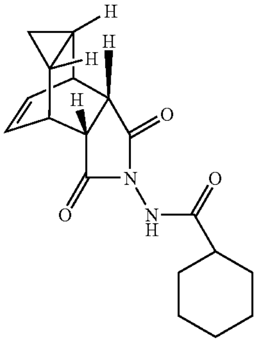 | N-(3,3a,4,4a,5,5a,6,6a-octahydro-1,3-dioxo-7,8-dimethyl-4,6-ethenocycloprop[f]isoindol-2(1H)-yl) cyclohexanecarboxamide |
| 37 | 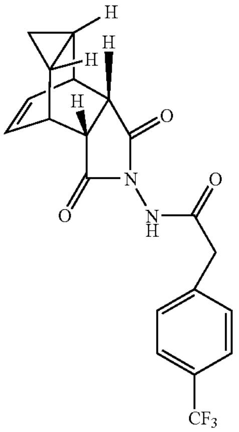 | 4-Trifluoromethyl-N-(3,3a,4,4a,5,5a,6,6a-octahydro-1,3-dioxo-7,8-dimethyl-4,6-ethenocycloprop[f]isoindol-2(1H)-yl)-benzylacetamide |
| 38 | 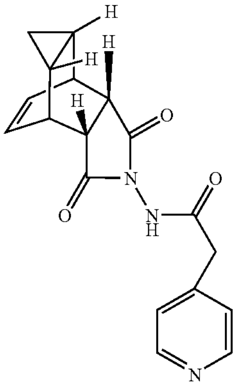 | 4-Pyridyl-N-(3,3a,4,4a,5,5a,6,6a-octahydro-1,3-dioxo-7,8-dimethyl-4,6-ethenocycloprop[f]isoindol-2(1H)-yl)-acetamide |
| 39 | 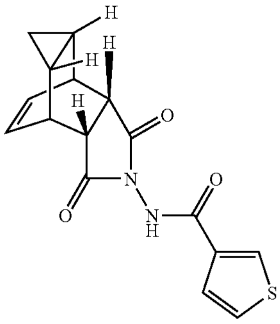 | 3-Thienyl-N-(3,3a,4,4a,5,5a,6,6a-octahydro-1,3-dioxo-7,8-dimethyl-4,6-ethenocycloprop[f]isoindol-2(1H)-yl)acetamide |

TABLE 2-continued

| | | |
|---|---|---|
| 40 | 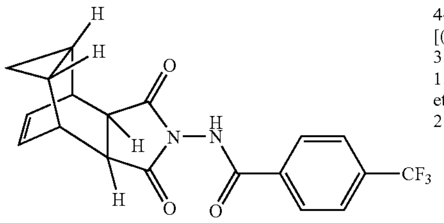 | 4-(Trifluoromethyl)-N-[(3aR,4S,4aS,5aR,6R,6aS)-3,3a,4,4a,5,5a,6,6a-octahydro-1,3-dioxo-4,6-ethenocycloprop[f]isoindol-2(1H)-yl]-4-benzamide |
| 41 | 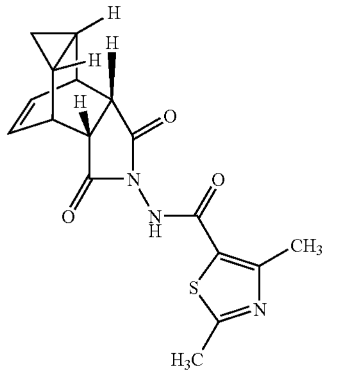 | 2,4-Dimethyl-N-(3,3a,4,4a,5,5a,6,6a-octahydro-1,3-dioxo-4,6-ethenocyclopropl[f]isoindol-2(1H)-yl)-thiazole-5-carboxamide |

Inhibition of Orthopox Viral Replication

The ability of the compounds described herein to inhibit Vaccinia virus was established by the following experimental procedure:

(a) Preparation of Virus Stock:

Virus stocks of Vaccinia virus (NYCBH) were prepared in Vero cells infected at low multiplicity (0.01 plaque forming units (PFU)/cell) and harvested when cytopathic effects were complete (4+CPE). The samples were frozen and thawed and then sonicated to release cell-associated virus. The cell debris was removed by low-speed centrifugation, and the resulting virus suspension was stored in 1 mL aliquots at −80° C. The PFU/mL of the virus suspension was quantified by standard plaque assay on Vero and BSC-40 cells.

(b) Vaccinia CPE: Assay:

To determine the amount of vaccinia virus stock required to produce complete CPE in 3 days, Vero cell monolayers were seeded on to 96-well plates and infected with 2-fold serial dilutions of the vaccinia virus stock. At 3 days post-infection, the cultures were fixed with 5% glutaraldehyde and stained with 0.1% crystal violet. Virus-induced CPE was quantified spectrophotometrically at $OD_{570}$. From this analysis, a 1:800 dilution of vaccinia virus stock was chosen for use in the HTS assay. This amount of vaccinia virus represents a multiplicity of infection of approximately 0.1 PFU/cell. To establish the signal-to-noise ratio (S/N) of the 96-well assay and evaluate the well-to-well and assay-to-assay variability, six independent experiments were performed. Vero cell monolayers were infected with 1:800 dilution of vaccinia virus stock. Each plate contained the following controls: quadruplicate virus-infected wells, quadruplicate uninfected cell wells and a dose response curve in duplicate for cidofovir (CDV) added at 300, 100, 30 and 10 DAM, or phosphonoacetic acid (PAA) added at 2100, 714, 210, and 71 M as reference standards. At day 3 post-infection, the plates were processed as described above.

The results of these experiments indicated that the 96-well assay format is robust and reproducible. The S/N ratio (ratio of signal of cell control wells (signal) to virus control wells (noise)) was 9.2±1.8. The well-to-well and assay-to-assay variability was less than 20%. Using this assay, the $EC_{50}$ values for CDV and PAA were determined to be 84±15 μM and 985±85 μM, respectively. These values were within the range of published values for these compounds. Based on this analysis, the 1:800 dilution of vaccinia virus (boxed) was chosen for use in the assay.

(c) Compound Testing:

Representative compounds of the invention were tested in the vaccinia virus CPE assay. Compounds were dissolved in DMSO and diluted in medium such that the final concentration in each well was 5 pM compound and 0.5% DMSO. The compounds were added robotically to the culture medium using the Biomek.RTM. FX robot system.

Following compound addition, the cultures were infected with vaccinia virus. After 3 days, plates were processed and CPE quantified as described.

Representative compounds of the invention inhibited vaccinia virus-induced CPE by greater than 50% at the test concentration (5 μM). Selected compounds were further evaluted for potency ($EC_{50}$) in the CPE assay and cytotoxicity ($CC_{50}$) in an MTT assay. The MTT assay measures mitochondrial dehydrogenase activity in dividing cells. This method detects the in situ reduction of (3-(4,5-dimethylthiazol-2-yl)-5-(3-carboxymethoxyphenyl)-2-(4-sulfophenyl- )-2H-tetrazolium) using an electron coupling reagent (phenazine methosulfate) to produce an insoluble formazan. The absorbance of the formazin at 490 nm can be measured directly from 96-well assay plates following solubilization of the formazan in 50% ethanol. The quantity of formazan product is directly proportional to the number of living cells in culture.

$EC_{50}$ values are determined by comparing compound-treated and compound-untreated cells using a computer program. (The $EC_{50}$ value measures compound concentration that inhibits viral replication by 50%). The $EC_{50}$ values of representative compounds of the invention in the CPE assay are listed in Table 3, below. These compounds were active at non-toxic concentrations.

TABLE 3

| Example Number | Vaccinia EC50 A = <0.5 μM, B = 0.5 to <1.0 μM, C = 1.0 to <5 μM, D = ≧5 μM | Cowpox EC50 A = <0.5 μM, B = 0.5 to <1.0 μM, C = 1.0 to <5 μM, D = ≧5 μM |
|---|---|---|
| 1 | A | A |
| 2 | A | C |
| 3 | A | B |
| 4 | A | C |
| 5 | B | B |
| 6 | B | D |
| 7 | A | *** |
| 8 | A | B |
| 9 | A | D |
| 10 | D | D |
| 11 | C | D |
| 12 | A | A |
| 13 | A | B |
| 14 | A | C |
| 15 | A | A |
| 16 | A | A |
| 17 | A | C |
| 18 | A | A |
| 19 | A | A |
| 20 | A | A |
| 21 | A | A |
| 22 | A | C |
| 23 | A | *** |
| 24 | A | B |
| 25 | B | D |
| 26 | A | *** |
| 27 | B | *** |
| 28 | A | A |
| 29 | A | A |
| 41 | A | C |

***Indicates that data were not collected.

Spectrum and Specificity of Activity of Compounds

Several additional CPE inhibition assays, similar to above, were utilized to identify a spectum of activity of compounds of the invention within the *orthopox* genus. For example, corresponding EC50 values of representative compounds in wild type cowpox virus (obtained from USAMRIID, Fort Detrick, Frederick, Md.) are listed in Table 3, above.

Table 4 lists $EC_{50}$ values of select compounds of the invention measuring anti-orthopox virus activities in these CPE inhibition assays for cidofovir-resistant cowpox virus (Brighton Red strain, (available from USAMRIID Fort Detrick, Frederick, Md.), camelpox, and monkeypox virus (Zaire (V79-1-005-scab)).

TABLE 4

| Example Number | Cidofovir-Resistant Cowpox $EC_{50}$ A = <0.5 μM, B = 0.5 to <1.0 μM, C = 1.0 to <5 μM, D = ≧5 μM | Monkeypox $EC_{50}$ A = <0.5 μM, B = 0.5 to <1.0 μM, C = 1.0 to <5 μM, D = ≧5 μM | Camelpox $EC_{50}$ A = <0.5 μM, B = 0.5 to <1.0 μM, C = 1.0 to <5 μM, D = ≧5 μM |
|---|---|---|---|
| 1 | A | A | A |
| 2 | A | A | A |
| 3 | A | A | A |
| 15 | A | A | A |
| 24 | B | A | A |

The specificity of representative compounds for orthopox virus inhibition is reflected in the fact that they do not inhibit the replication of unrelated viruses, including Pichinde virus, Rift Valley fever virus (strain MP12), respiratory syncytial virus and cytomegalovirus.

EXAMPLE 42

CHARACTERIZATION OF 4-trifluoromethyl-N-(3,3a,4,4a,5,5a,6,6a-octahydo-1,3-dioxo-4,6-ethenocycloprop[f]isoindol-2(1 H)-yl)-benzamide ("ST-246")

Physico-chemical Properties

Appearance: ST-246 is a white to off-white powder.

Melting Point: Approximately 196° C. by DSC.

Permeability: The calculated log P is 2.94. Based on the partition coefficient, ST-246 is expected to have good permeability.

Particle Size: The drug substance is micronized to improve its dissolution in the gastrointestinal fluids. The typical particle size of the micronized material is 50% less than 5 microns.

Solubility: The solubility of ST-246 is low in water (0.026 mg/mL) and buffers of the gastric pH range. Surfactant increases its solubility slightly. ST-246 is very soluble in organic solvents. The solubility data are given in Table 5.

TABLE 5

Solubility of ST-246 in Various Diluents

| Diluent | ST-246 Solubility (mg/mL) |
|---|---|
| Phosphate Buffer, pH 6.8 | 0.00700 |
| Water | 0.0261 |
| 0.01N HCl | 0.0375 |
| 1% Sodium Laurel Sulfate | 0.0687 |
| 1% Tween 80 ® | 0.102 |
| Methanol | 60.8 |
| Ethanol | 62.1 |
| Acetonitrile | 64.0 |

Polymorphism: X-ray diffraction pattern indicated crystalline material and is similar for various batches. DSC shows sharp endotherms at 196° C. corresponding to the melting point. There are small endotherms between 115 C. and 189° C. The position of these endotherms varies in the two batches.

Biopharmaceutical Classification: ST-246 is classified as BCS Class 2 due to its low solubility in solutions of gastric pH range and good permeability.

Stability: Short-term forced degradation studies indicated that ST-246 has good stability in solid state, and in neutral, acidic, and basic (50:50 water/acetonitrile) solutions. Small amounts of degradation products were formed.

The micronized ST-246 GMP batch 06-0503 16-04/04-24-0 1 (Batch # Micronized 5C020) intended for clinical trial was placed on a three-year stability program in the current container (amber glass bottles) according to International Conference for Harmonization (ICH) guidelines. Six-month data indicate that ST-246 is stable at 25° C./60% RH and 40° C./75% RH and light.

There is no time or temperature dependent change in appearance, moisture, assay, impurities, and XRD. The DSC patterns at 2 months at 25OC/60% RH and 3 months at 40° C./75% RH show slight differences from that of the initial sample. From cyclic DSC and TGA analysis, it appears that the initial sample has a mixture of free and bound water as indicated by a broad endotherm at 115° C. (100-130° C.), and changes to bound water as indicated by a shift of this endotherm to 131-134° C. TGA shows loss of 2% water at 126° C.

EXAMPLE 43

Process for Manufacturing 4-Trifluoromethyl-N-(3,3a,4,4a,5,5a,6,6a-octahydro-1,3-dioxo-4,6-etheneo-cyclopropyl[f]isoindol-2(1H)-yl)-benzamide ("ST-246")

ST-246 may be manufactured in a process comprising the following four steps:

Step 1: A solution of cycloheptatriene (1) and maleic anhydride (2) in anhydrous toluene is heated at 80° for 4 hours under a nitrogen atmosphere. After GC/MS analysis shows the reactions is complete, the reaction solution is cooled to room temperature and evaporated under reduced pressure. The resulting residue is recrystallized from tert-butyl methyl ether to afford the endo-isomer (3) as a white crystal.

Step 2: To a solution of anhydrous hydrazine in anhydrous toluene is added methyl 4-(trifluoromethyl) benzoate (4). The reaction solution is heated at reflux for 18 hours under a nitrogen atmosphere. After cooling to 40-50° C., the solvent is evaporated under reduced pressure. The resulting solid is recrystallized from tert-butyl methyl ether to give hydrazide (5) as a white solid.

Step 3: A mixture of the endo-isomer (3), the hydrazide (5), and ethanol is heated at reflux for 18 hours under a nitrogen atmosphere. The resulting solution is cooled to room temperature and concentrated in vacuo. The crude material (6) is used directly for the next step.

Step 4: The crude material (6) is recrystallized from ethyl acetate and hexanes to obtain ST-246 (7) as a white solid. The material is dried for 48 hours at 40° C.

For storage, the material may be packaged in amber glass bottles and stored at 2 to 8° C.

EXAMPLE 44

Characterization of ST-246

The physical form for ST-246 is a white to off-white solid. The molecular formula is $C_{19}H_{15}F_3N_2O_3$. The molecular weight is 376.33. The melting point is 196° C. by DSC. The solubility of ST-246 is low in water (0.026 mg/mL) and slightly in buffers of the gastric pH range. ST-246 is very soluble in organic solvents (60 mg/mL). The chemical structure is shown in Table 1 (Example 1).

The structure of ST-246 was elucidated using elemental analysis, infrared spectroscopy, ultraviolet spectroscopy, mass spectroscopy, proton nuclear magnetic resonance spectroscopy, and DSC. Elemental analysis was carried out on the following elements: carbon, hydrogen, fluorine, nitrogen, and oxygen. The results of the analysis are given below in Table 6. The elemental analysis results are consistent with ST-246 containing 0.235 moles of water.

TABLE 6

Elemental Analysis of ST-246

| Element | Expected As Anhydrous | Expected With 0.235 Moles of Water | Found | Std. Dev. |
|---|---|---|---|---|
| C | 60.64 | 59.97 | 59.97 | 0.3 |
| H | 4.02 | 4.1 | 4.02 | 0.1 |
| F | 15.15 | 14.98 | 14.94 | 0.1 |
| N | 7.44 | 7.36 | 7.36 | 0.05 |
| O | 12.75 | 13.66 | 13.71 | 0.19 |

Short-term forced degradation studies indicate that ST-246 has good stability in the solid state and in neutral, acidic, and basic (50:50 water/acetonitrile) solutions. Small amounts of degradation products were formed.

A three-month long test of the stability of ST-246 has been conducted. Storage for three months at 40° C./75% RH and 25° C./65% RH conditions showed no change in the analytical results of any of the parameters tested.

EXAMPLE 44

Formulation of ST-246

ST-246 can be formulated for oral administration in, for example, size 0 capsules containing either 25 mg or 200 mg ST-246. All inactive ingredients may be GRAS and USPLNF excipients. The manufacturing process may include wet granulation using a high shear mixer/granulator and filling into hard-gelatin capsules.

Exemplary Components

Microcrystalline cellulose, NF (Avicel PH 101)
Lactose monohydrate, spray dried, NF, (Fast-flo)
Croscarmellose sodium, NF (Ac-Di-Sol)
Hydroxypropylmethyl cellulose, USP (Methocel E3)
Sodium lauryl sulfate (SLS), NF
Colloidal silicone dioxide, NF (Cab-0-Sil M5P)
Magnesium stearate, NF (Non-bovine)
Purified water, USP
Hard gelatin capsule opaque white size 0

Description and Quantitative Composition

Suitable dosage forms include capsules containing various amounts of active ingredient. The quantitative composition of two exemplary dosage forms containing 25 or 200 mg of ST-246 are listed below in Table 6.

TABLE 6

Quantitative Composition for ST-246 Drug Product

| Ingredient | Function | 200 mg strength mg/Capsule | 200 mg strength % w/w | 25 mg strength mg/Capsule | 25 mg strength % w/w |
|---|---|---|---|---|---|
| ST-246[a] | Active Ingredient | 200.00 | 51.28 | 25.00 | 7.14 |
| Microcrystalline cellulose, NF[b] | Water Insoluble Diluent | 88.60 | 22.72 | 144.76 | 41.36 |
| Lactose monohydrate, NF | Water soluble Diluent | 33.15 | 8.50 | 119.0 | 34.0 |
| Croscarmellose sodium, NF[b] | Disintegrant | 42.90 | 11.00 | 38.5 | 11.00 |
| Colloidal silicon dioxide, NF | Glidant | 1.95 | 0.50 | 1.75 | 0.50 |
| Hydroxypropyl methylcellulose, USP | Binder | 13.65 | 3.50 | 12.25 | 3.50 |
| Sodium lauryl sulfate, NF | Wetting Agent/ Solubilizer | 7.80 | 2.00 | 7.0 | 2.00 |
| Purified water[c], USP | Granulating solvent | | | | |
| Magnesium stearate NF | Lubricant | 1.95 | 0.50 | 1.75 | 0.50 |
| Tablet weight | | 390 | 100 | 350 | 100 |

[a]The quantity of ST-246 may be adjusted based on the drug substance lot factor, which is calculated to reflect the purity along with the water and residual solvents content. A correspondingly reduced amount of microcrystalline cellulose will be adjusted to maintain the same capsule weight.
[b]Microcrystalline cellulose and croscarmellose sodium are added as intragranular and extragranular excipients.
[c]Removed during processing.

Typical Batch Formula

Batch sizes may vary. Formulas for typical batch sizes are listed below in Table 7.

TABLE 7

| Excipients | 200 mg Capsules g per 2400 g Batch | 25 mg Capsules g per 800 g Batch |
|---|---|---|
| ST-246, micronized* | 1230.9 | 57.14 |
| Microcrystalline cellulose, NF (Avicel PH101) | 545.1 | 330.88 |
| Lactose monohydrate, NF (Fast Flo) | 204.0 | 272.00 |
| Croscarmellose sodium, NF (Ac-Di-Sol) | 264.0 | 88.00 |
| Hydroxypropylmethyl cellulose, USP (Methocel E3) | 84.0 | 28.00 |
| Sodium lauryl sulfate, NF | 48.0 | 16.00 |
| Colloidal silicone dioxide, NF (Cab-0-Sil M5P) | 12.0 | 4.00 |
| Magnesium stearate, NF (Non-bovine) | 12.0 | 4.00 |
| Purified water**, USP | — | — |
| Total Weight | 2400 | 800 |
| Capsules, empty, hard gelatin, size 0, white/white opaque | 6000 Capsules | 2285 Capsules |

*The quantity of ST-246 may be adjusted based on the drug substance lot factor, which is calculated to reflect the purity along with the water and residual solvents content. A corresponding reduced amount of microcrystalline cellulose will be adjusted to maintain the same fill weight per capsule.
**Removed during drying.

Step-Wise Manufacturing Procedure

A stepwise process for the manufacture of ST-246 25 mg and 200 mg capsules, is listed below.

1. Dissolve sodium lauryl sulfate and hydroxypropylmethyl cellulose in purified water.
2. Sift through 20-mesh screen and mix ST-246, microcrystalline cellulose, croscarmellose sodium, lactose, and colloidal silicone dioxide at slow speed in high shear mixer.
3. Add sodium lauryl sulfate and hydroxypropylmethyl cellulose solution while mixing.
4. Mix at slow speed after addition of solution.
5. Add more purified water if needed and mix.
6. Dry in the fluid bed dryer.
7. Pass the dried granulation through #30 mesh screen. Pass the granulation remaining on top of #30 mesh screen using comil.
8. Weigh the granulation and calculate quantities of the extra-granular excipient.
9. Add milled granulation into a V-blender and add croscarmellose sodium and microcrystalline cellulose (pre-screened through 20-mesh) to the blender, and mix. Take a portion of the blend and mix with magnesium stearate, add to the blender and mix.
10. Fill into capsules.

One of ordinary skill will readily be able to modify this process in order to accommodate different amounts of ST-246 per dose as required.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A process for producing ST-246

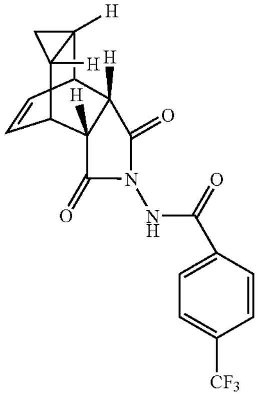

of the formula comprising the steps of:

a) heating a mixture of anti-tricyclo[3.2.2.0]non-6-ene-endo-8, endo-9-dicarboxylic acid anhydride, 4-(trifluoromethyl)benzhydrazide, and ethanol at reflux to form a solution;
b) cooling the solution;
c) concentrating the solution to form a residue; and
d) recrystallizing the residue from ethyl acetate and hexanes to obtain ST-246.

2. The process of claim 1, wherein the mixture of step (a) is heated for about 18 hours.

3. The process of claim 1, wherein the mixture of step (a) is heated under an inert atmosphere.

4. The process of claim 3, wherein the inert atmosphere consists essentially of nitrogen.

5. The process of claim 3, wherein the inert atmosphere consists essentially of argon.

6. The process of claim 1, wherein the cooling of step (b) is to about room temperature.

7. The process of claim 1, wherein the solution is concentrated under reduced pressure.

8. The process of claim 7, wherein the reduced pressure of step (c) is a vacuum.

9. The process of claim 1, wherein the solution is concentrated by rotary evaporation.

10. A process for producing ST-246

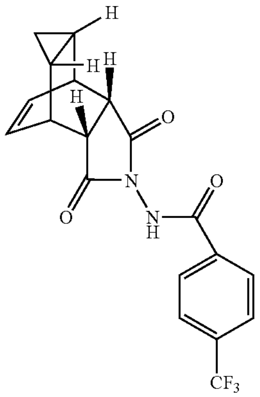

of the formula comprising the steps of:

heating a mixture of anti-tricyclo[3.2.2.0]non-6-ene-endo-8, endo-9-dicarboxylic acid anhydride, 4-(trifluoromethyl)benzhydrazide, and ethanol at reflux for 18 hours under a nitrogen atmosphere to form a solution;
cooling the solution to room temperature;
concentrating the solution in vacuo to form a residue; and
recrystallizing the third residue from ethyl acetate and hexanes to obtain ST-246.

* * * * *

UNITED STATES PATENT AND TRADEMARK OFFICE

CERTIFICATE OF CORRECTION

PATENT NO. : 7,687,641 B2
APPLICATION NO. : 11/785997
DATED : March 30, 2010
INVENTOR(S) : Robert Jordan et al.

It is certified that error appears in the above-identified patent and that said Letters Patent is hereby corrected as shown below:

In column 1, after line 21, please add the following new paragraph:

STATEMENT REGARDING FEDERALLY SPONSORED RESEARCH OR DEVELOPMENT

This invention was made with U.S. Government support under Contract No. HHSN266200600014C awarded by the National Institute of Health (NIH). The U.S. Government has certain rights in the invention.

Signed and Sealed this
Fourteenth Day of June, 2011

David J. Kappos
*Director of the United States Patent and Trademark Office*